US011229455B2

(12) United States Patent
Ikeuchi et al.

(10) Patent No.: US 11,229,455 B2
(45) Date of Patent: Jan. 25, 2022

(54) INSTRUMENT FOR FIXEDLY TRANSPLANTING LIVING BODY EMBRYO INTO UTERUS

(71) Applicants: THE UNIVERSITY OF TOKYO, Tokyo (JP); ST. MARIANNA UNIVERSITY SCHOOL OF MEDICINE, Kawasaki (JP); KITAZATO CORPORATION, Fuji (JP)

(72) Inventors: Masashi Ikeuchi, Tokyo (JP); Kazuhiro Kawamura, Tokyo (JP); Futoshi Inoue, Fujinomiya (JP)

(73) Assignees: THE UNIVERSITY OF TOKYO, Tokyo (JP); ST. MARIANNA UNIVERSITY SCHOOL OF MEDICINE, Kawasaki (JP); KITAZATO CORPORATION, Fuji (JP)

( * ) Notice: Subject to any disclaimer, the term of this patent is extended or adjusted under 35 U.S.C. 154(b) by 275 days.

(21) Appl. No.: 16/511,540

(22) Filed: Jul. 15, 2019

(65) Prior Publication Data
US 2019/0336169 A1 Nov. 7, 2019

Related U.S. Application Data

(63) Continuation of application No. PCT/JP2018/001046, filed on Jan. 16, 2018.

(30) Foreign Application Priority Data

Jan. 17, 2017 (JP) .............................. JP2017-006174

(51) Int. Cl.
*A61B 17/435* (2006.01)
*A61D 19/04* (2006.01)
(Continued)

(52) U.S. Cl.
CPC .. *A61B 17/435* (2013.01); *A61B 2017/00876* (2013.01); *A61D 19/04* (2013.01); *A61M 31/00* (2013.01); *A61M 2210/1433* (2013.01)

(58) Field of Classification Search
CPC ..... A61B 17/425; A61B 17/43; A61B 17/435; A61B 5/0036; A61B 5/004; A61B 5/0043;
(Continued)

(56) References Cited

U.S. PATENT DOCUMENTS 5,626,148 A * 5/1997 Lehtinen .................. A61F 6/14
128/830
6,050,935 A 4/2000 Ranoux et al.
(Continued)

FOREIGN PATENT DOCUMENTS

CN 203555860 U 4/2014
JP 2003530129 A 10/2003
(Continued)

OTHER PUBLICATIONS

International Search Report (PCT/ISA/210) dated Mar. 13, 2018, by the Japan Patent Office as the International Searching Authority for International Application No. PCT/JP2018/001046.
(Continued)

*Primary Examiner* — Carrie R Dorna
(74) *Attorney, Agent, or Firm* — Buchanan Ingersoll & Rooney PC

(57) ABSTRACT

An instrument for fixedly transplanting a living body embryo into a uterus has an instrument, for transplanting the living body embryo into the uterus, which is to be inserted into a uterus and a magnetic embryo accommodation container holding instrument (transferred embryo fixing instrument) to be attached to the living body. The instrument for transplanting the living body embryo into the uterus has an
(Continued)

embryo accommodation container having an embryo accommodation part having an embryo insertion portion communicating with outside and a magnetic material and a shaft-shaped container transfer tool for separably holding the embryo accommodation container at its distal end portion. The magnetic container holding instrument has an attaching part to be attached to an epidermis of the living body and a magnet capable of attracting the magnetic material of the embryo accommodation container thereto.

13 Claims, 22 Drawing Sheets

(51) Int. Cl.
*A61B 17/00* (2006.01)
*A61M 31/00* (2006.01)

(58) Field of Classification Search
CPC ... A61B 5/0046; A61B 5/0069; A61B 5/0076; A61B 5/0083; A61D 19/00; A61D 19/04; A61F 6/14; A61F 6/142; A61F 6/144; A61F 6/146; A61F 6/148; A61F 6/16
See application file for complete search history.

(56) References Cited

U.S. PATENT DOCUMENTS

| | | | |
|---|---|---|---|
| 6,656,194 B1 * | 12/2003 | Gannoe | A61F 5/0003 604/96.01 |
| 8,333,688 B2 | 12/2012 | Mock et al. | |
| 2003/0204128 A1 * | 10/2003 | Moruzzi | C12N 5/0006 600/34 |
| 2004/0261799 A1 | 12/2004 | Mock | |
| 2009/0012352 A1 | 1/2009 | Mock et al. | |
| 2009/0299129 A1 | 12/2009 | Mock et al. | |
| 2011/0275885 A1 | 11/2011 | Bouche | |
| 2016/0008030 A1 | 1/2016 | Buster et al. | |
| 2017/0119513 A1 | 5/2017 | Decherf et al. | |

FOREIGN PATENT DOCUMENTS

| | | |
|---|---|---|
| JP | 2005508210 A | 3/2005 |
| JP | 2009521296 A | 6/2009 |
| JP | 2009544348 A | 12/2009 |
| JP | 2011512219 A | 4/2011 |
| WO | 03/090632 A1 | 11/2003 |
| WO | 2015185863 A1 | 12/2015 |

OTHER PUBLICATIONS

Written Opinion (PCT/ISA/237) dated Mar. 13, 2018, by the Japan Patent Office as the International Searching Authority for International Application No. PCT/JP2018/001046.
The extended European Search Report dated Aug. 12, 2020, by the European Patent Office in corresponding European Patent Application No. 18741882.7-1122. (7 pages).

* cited by examiner

INSTRUMENT FOR FIXEDLY TRANSPLANTING LIVING BODY EMBRYO INTO UTERUS

TECHNICAL FIELD

The present invention relates to an instrument for fixedly transplanting a living body embryo into a uterus. More specifically, the present invention relates to an instrument for transplanting an embryo of a mammal into a uterus and holding the transplanted embryo at an appropriate portion inside the uterus until the transplanted embryo implants on the endometrium.

BACKGROUND ART

Recently owing to the factor that the age at which women bear children is rising, assisted reproductive technology is being increasingly performed. Above all, in-vitro fertilization is being increasingly performed. There is a report that the in-vitro fertilization was performed in excess of 350,000 in the year of 2013. The in-vitro fertilization means that after an ovum taken out of a utilizer's ovary is fertilized with a sperm outside her body and is cultured for a certain period of time, a generated embryo is transplanted into a uterus by using an embryo transplantation instrument.

A fertilized ovum grows into a quaternary embryo in about 24 hours, an eight-split embryo in about another 24 hours, thereafter a fertile embryo, and a blastocyst. Although it is possible to transplant the fertile embryo and the blastocyst into the uterus, the quaternary embryo and the eight-split embryo are more often utilized than the fertile embryo and the blastocyst in transplanting them into the uterus because the operation of transplanting the former into the uterus can be performed more easily than the operation of transplanting the latter thereinto. None of the embryos implant on an endometrium immediately after the embryos are transplanted thereon, but a certain period of time is required for them to implant thereon. The embryos are movable in the living body until they implant thereon. The movement of the embryo to the vicinity of an oviduct is the factor of ectopic pregnancy, while the movement thereof to the vicinity of the opening of the uterus is the factor of placenta previa. It is desirable to hold the transplanted embryo until it implants on an appropriate portion of the uterus.

In Japanese Translation of PCT International Application Publication No. 2011-512219 (patent document 1), the recoverable intra-uterine system was proposed. The recoverable intra-uterine system disclosed in the patent document 1 comprises a receptacle (10) designed to contain one or more elements chosen from the group comprising an embryo, male and/or female gametes, a fertilized oocyte, an unfertilized ovum, and a combination of these elements, and a retaining device (20) for retaining the recoverable intra-uterine system in the uterus. The retaining device (20) comprises a deformable element (21) designed to be retained by bearing in the neck of the uterus.

In Japanese Translation of PCT International Application Publication No. 2009-544348 (patent document 2), the recoverable intra-uterine system was also proposed. The recoverable intra-uterine system disclosed in the patent document 2 comprises a housing (10) capable of containing one or a plurality of elements selected from among the group comprising an embryo, male and/or female gametes, a fertilized oocyte, and unfertilized ovum and a combination of these elements, the housing (10) having along an axis (X) a distal end (12) and a proximal end (13), and a device (20) for holding the recoverable intra-uterine device in the uterus. The holding device (20) is arranged at the proximal end (13) of the housing (10) and includes at least one holding arm (23) in the uterine cavity capable of taking at least two positions: one free position in which at least one holding arm (23) is separated from the axis (X); and a retracted position in which at least one holding arm (23) is substantially parallel to the axis (X).

In Japanese Translation of PCT International Application Publication No. 2009-521296 (patent document 3), the embryo transplantation instrument was disclosed. The embryo transplantation instrument disclosed in the patent document 3 is the collectable intrauterine instrument comprising a housing (11) containing one or several elements selected from a group containing an embryo, male and/or female gametes, a fertilised oocyte, an unfertilised egg and the combination thereof, wherein said housing (11) is provided with a wall made of a biocompatible material. The wall is provided with a series of perforations (12, 12') whose size is sufficient in order to bring the intra-uterine medium into a cellular contact with the housing (11) and to keep the elements therein. The inventive device is provided with a system for loading and unloading one or several elements selected from the group containing an embryo, male and/or female gametes, a fertilised oocyte, an unfertilised egg and the combination thereof.

PRIOR ART DOCUMENTS

Patent Documents

Patent document 1: Japanese Translation of PCT International Application Publication No. 2011-512219 (US Patent Application Publication No. 2011-275885)

Patent document 2: Japanese Translation of PCT International Application Publication No. 2009-544348 (US Patent Application Publication No. 2009-299129, U.S. Pat. No. 8,333,688)

Patent document 3: Japanese Translation of PCT International Application Publication No. 2009-521296 (US Patent Application Publication No. 2009-012352)

SUMMARY OF THE INVENTION

Problems to be Solved by the Invention

Although intrauterine systems disclosed in the patent documents 1 and 2 are collectable from the uterus, the intrauterine instruments have a certain degree of size. Thus, it is not easy to perform the operation of disposing the intrauterine instruments inside the uterus and collecting them from the inside of the uterus. The intrauterine instruments are placed inside the uterus for a certain period of time, although they are not placed for a long period of time. Therefore, they give a sense of uncomfortableness to utilizers. In the case of the intrauterine instrument disclosed in the patent document 3, how to perform an operation of disposing the intrauterine instrument inside the uterus and collecting it from the inside of the uterus is unclear.

It is an object of the present invention to provide an instrument, for fixedly transplanting a living body embryo into a uterus, which is capable of easily transferring an embryo to an appropriate portion inside a uterus and holding the transferred embryo at the appropriate portion inside the uterus.

Means for Solving the Problems

The above-described object can be achieved by an instrument for fixedly transplanting a living body embryo into a uterus described below achieves.

The instrument for fixedly transplanting the living body embryo into the uterus comprises a living body embryo transplanting device having an embryo accommodation container and inserting into the uterus, and a magnetic embryo accommodation container holding device, to be attached to a living body, for magnetically attracting the embryo accommodation container thereto. The embryo accommodation container has an embryo accommodation part having an embryo insertion portion communicating with outside, and a magnetic material. The living body embryo transplanting device into the uterus has a shaft-shaped container transfer tool for separably holding the embryo accommodation container at a distal end portion of the container transfer tool. The magnetic embryo accommodation container holding device has an attaching part to be attached on a living body epidermis and a magnet capable of attracting the magnetic material of the embryo accommodation container.

MODE FOR CARRYING OUT THE INVENTION

Figure 1:
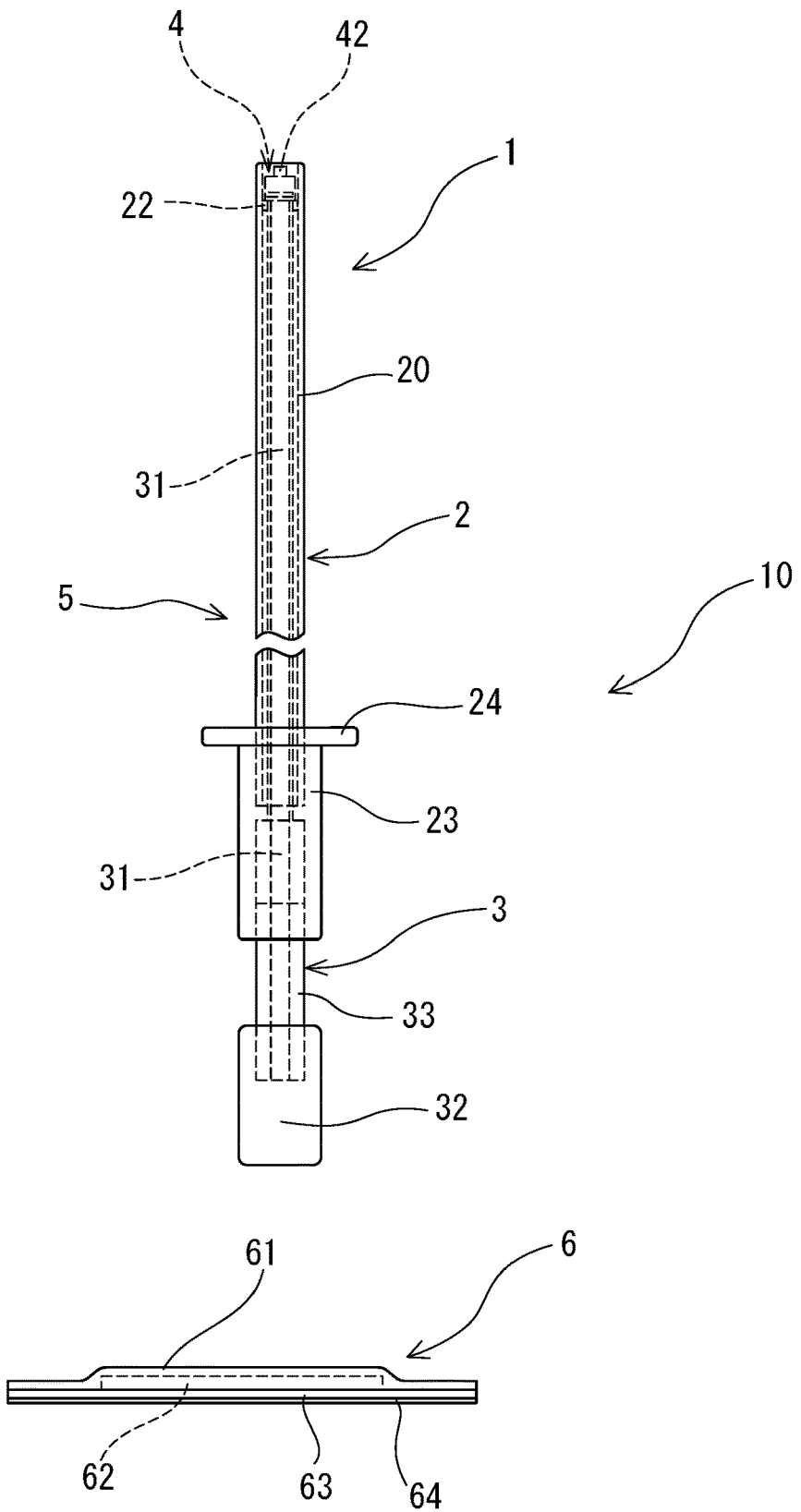
FIG. 1 is a front view of one embodiment of an instrument of the present invention for fixedly transplanting a living body embryo into a uterus.

By using the embodiments shown in the drawings, description is made below on an instrument of the present invention for fixedly transplanting a living body embryo into a uterus.

An instrument 10 of the present invention for fixedly transplanting the living body embryo into the uterus has a living body embryo transplanting device 1, which is to be inserted into the uterus, and a magnetic embryo accommodation container holding device (transferred embryo fixing device) 6 to be attached to a living body. The living body embryo transplanting device 1 into the uterus has an embryo accommodation container 4 having an embryo accommodation part 42 having an embryo insertion portion 44 communicating with the outside and a magnetic material 43 and a shaft-shaped container transfer tool 5 for separably holding the embryo accommodation container 4 at its distal end portion. The magnetic container holding device 6 has an attaching part 63 to be attached to an epidermis of the living body and a magnet 62 capable of attracting the magnetic material 43 of the embryo accommodation container 4 thereto.

The instrument 10, shown in FIGS. 1 through 5 and FIG. 14, for fixedly transplanting the living body embryo into the uterus is described below.

The instrument 10 for fixedly transplanting the living body embryo into the uterus has the living body embryo transplanting device 1 into the uterus and the magnetic embryo accommodation container holding device 6.

The living body embryo transplanting device 1 into the uterus has the embryo accommodation container 4 and the container transfer tool 5.

Figure 3:
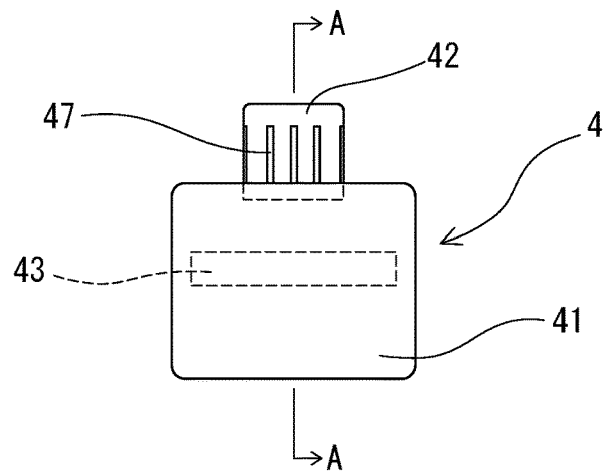
FIG. 3 is an enlarged front view of an embryo accommodation container for use in the instrument for fixedly transplanting the living body embryo into the uterus shown in FIG. 1.
Figure 4:
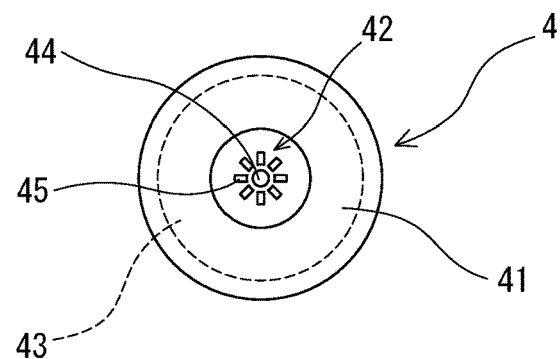
FIG. 4 is a plan view of the embryo accommodation container shown in FIG. 3.
Figure 5:
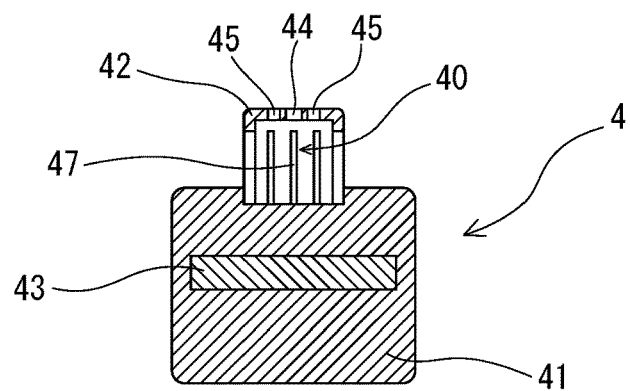
FIG. 5 is a sectional view taken along an A-A line of FIG. 3.

As shown in FIGS. 3 through 5, the embryo accommodation container 4 of the embodiment shown in the above-described drawings has the embryo accommodation part 42 having an embryo accommodation space 40 inside it and a body part 41. In the embryo accommodation container 4 of this embodiment, the embryo accommodation part 42 is fixed to an upper surface of the body part 41.

The embryo accommodation part 42 has the embryo insertion portion (embryo insertion opening) 44 allowing the outside and the embryo accommodation space 40 to communicate with each other.

The embryo accommodation container 4 of the embodiment is provided with openings 47, formed on a side surface of the embryo accommodation part 42 thereof, which allows the outside and the embryo accommodation space 40 to communicate with each other. The openings 47 enable the circulation of a liquid (biological liquid). A plural number of the openings 47 are formed on the side surface of the embryo accommodation part. In the embryo accommodation container 4 of this embodiment, each of the openings 47 is composed of a narrow window portion extended in the axial direction of the embryo accommodation part 42. The embryo accommodation container 4 is also provided with a plurality of openings 45 formed on an upper surface of its embryo accommodation part 42. Each of the openings 45 formed on the upper surface of the embryo accommodation part for circulating the biological liquid is formed of a window portion extended from a central side of the upper surface of the embryo accommodation part toward a peripheral side of the upper surface thereof.

The embryo accommodation container 4 of this embodiment is provided with the embryo insertion portion 44 formed on its upper surface. The embryo insertion portion 44 is almost circular. Thus, an embryo can be easily inserted into the embryo accommodation container. A maximum diameter (diameter) of the embryo insertion portion 44 is set larger than the width of each of the above-described openings 45 and 47. In other words, the width of each of the openings 45 and 47 is smaller than the diameter of the embryo insertion portion 44. Thereby, it is possible to prevent the embryo from unintentionally flowing out of the embryo accommodation part 42.

The embryo accommodation container 4 has the magnetic material 43. The embryo accommodation container 4 may be formed entirely of the magnetic material. In this embodiment, the embryo accommodation container 4 is formed of synthetic resin. The magnetic material 43 is embedded inside the synthetic resin. The magnetic material 43 may be fixed to the surface of the embryo accommodation container 4.

The magnetic material 43 of the embryo accommodation container 4 of this embodiment is flat. More specifically, the disk-shaped magnetic material 43 is used. The embryo accommodation part 42 is cylindrical. The body part 41 is columnar. The embryo accommodation part 42 may be elliptically cylindrical or rectangularly cylindrical. The body part 41 may be elliptically columnar or rectangularly columnar.

As the magnetic material 43, a magnet made of iron, magnetic stainless, and a permanent magnet are used. As the magnetic material 43, the permanent magnet is preferable. The permanent magnet having a sufficiently high magnetic force is preferable. A neodymium magnet, a platinum magnet, an alnico magnet, and a samarium cobalt magnet are preferable.

In the embryo accommodation container 4 of this embodiment, the body part 41 has a larger diameter than the embryo accommodation part 42. Because the magnetic material 43 is disposed inside the body part 41, the magnetic material is sufficiently large. In the embryo accommodation container, the magnetic material may be fixed to the lower surface of the embryo accommodation part or the upper surface thereof.

Figure 10:
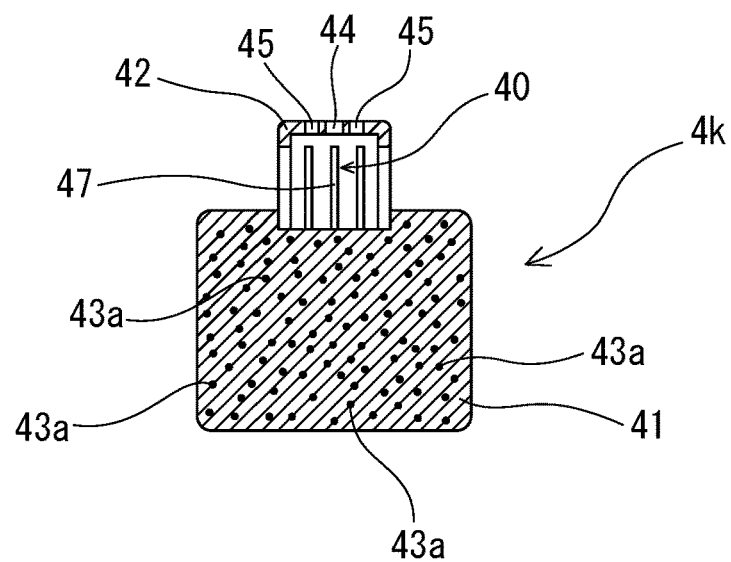
FIG. 10 is an enlarged vertical longitudinal sectional view of an embryo accommodation container of still another embodiment for use in the instrument of the present invention for fixedly transplanting the living body embryo into the uterus.

The size of the magnetic material is not limited to a certain extent unlike the above-described embodiment, but a large number of minute magnetic materials may be used. As the minute magnetic material, it is possible to use powders and particles of the magnetic material. An embryo accommodation container 4k of an embodiment shown in FIG. 10, namely, a body part of the embryo accommodation container contains a large number of minute magnetic particles 43a. The volume content rate at a part of the embryo accommodation container in which the minute magnetic particles are contained is preferably 0.1 to 5 vol % and especially preferably 0.5 to 3 vol %.

Figure 6:
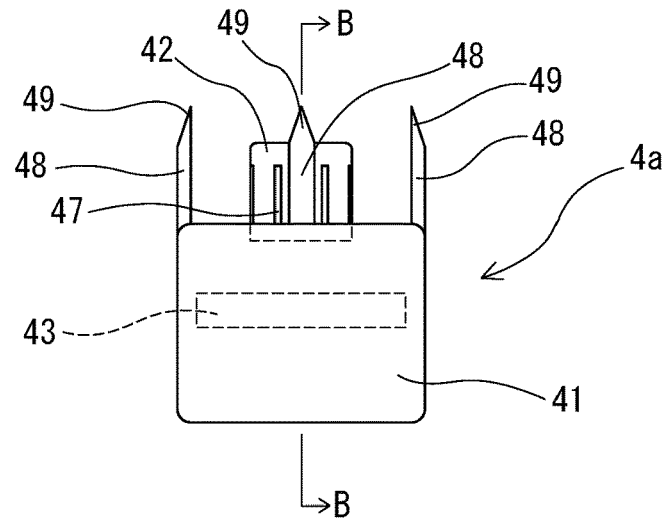
FIG. 6 is an enlarged front view of an embryo accommodation container of another embodiment for use in the instrument of the present invention for fixedly transplanting the living body embryo into the uterus.
Figure 7:
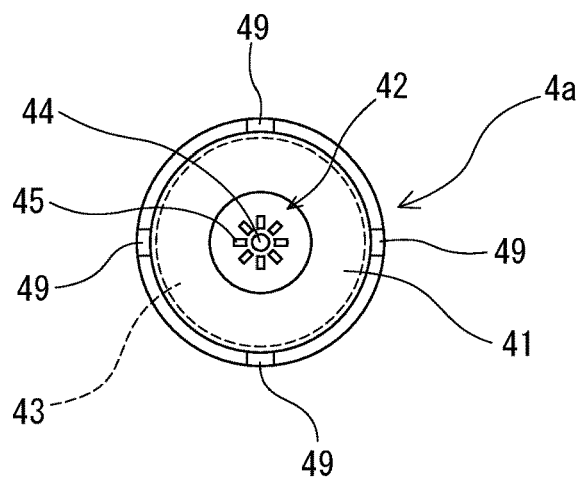
FIG. 7 is a plan view of the embryo accommodation container shown in FIG. 6.
Figure 8:
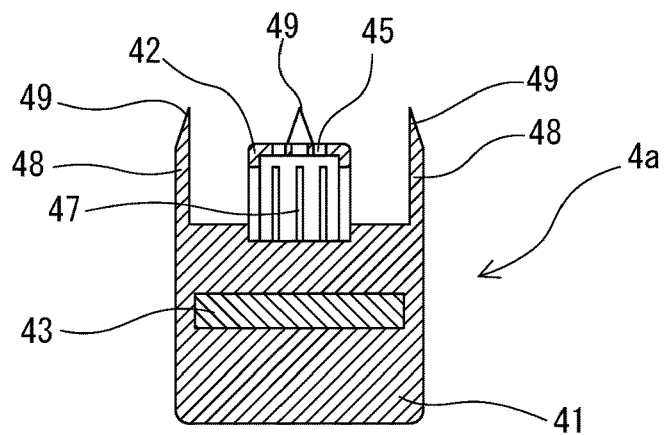
FIG. 8 is a sectional view taken along a B-B line of FIG. 6.

As with an embryo accommodation container 4a of an embodiment shown in FIGS. 6 through 8, the embryo accommodation container may have leg portions 48 to be attached to an endometrium. The embryo accommodation container 4a of this embodiment has a plurality of leg portions 48 projecting from a distal end of the body part 41. A pointed end portion 49 is formed at a distal end of each of the leg portions 48. The pointed end portion of the leg portion 48 is positioned distally from the embryo accommodation part 42.

In this embodiment, a plurality of the leg portions 48 is formed in such a way as to surround the embryo accommodation part 42. More specifically, the embryo accommodation container is provided with four leg portions. The number of the leg portions 48 to be formed is preferably 3 to 12 and especially preferably 3 to 6. The pointed end portion 49 is sharp.

Figure 9:
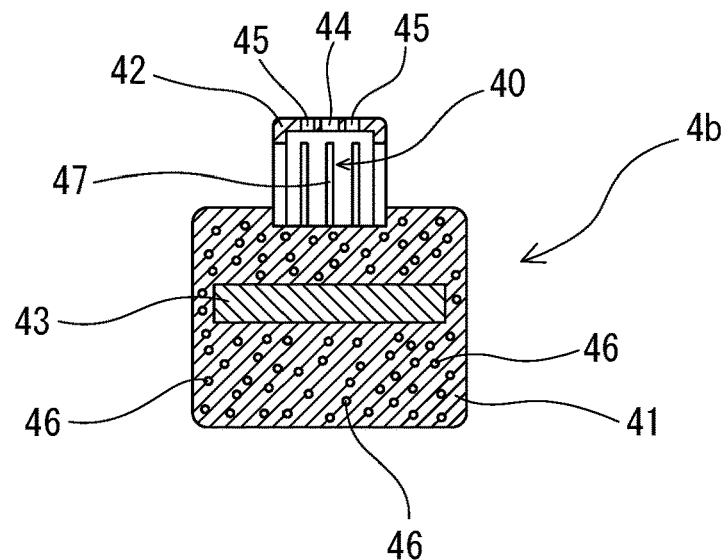
FIG. 9 is an enlarged vertical longitudinal sectional view of an embryo accommodation container of still another embodiment for use in the instrument of the present invention for fixedly transplanting the living body embryo into the uterus.

As with an embryo accommodation container 4b of an embodiment shown in FIG. 9, the embryo accommodation container may contain a large number of bubbles 46. By allowing the embryo accommodation container to contain bubbles 46, it becomes easy to facilitate recognition by ultrasonic wave imaging. The volume content rate of bubbles at a bubble containing part of the embryo accommodation container is preferably 0.1 to 5 vol % and especially preferably 0.5 to 3 vol %. The sectional area of a bubble is favorably 0.0001 to 1.0 $mm^2$, more favorably 0.001 to 0.8 $mm^2$, and most favorably 0.01 to 0.3 $mm^2$.

Figure 11:
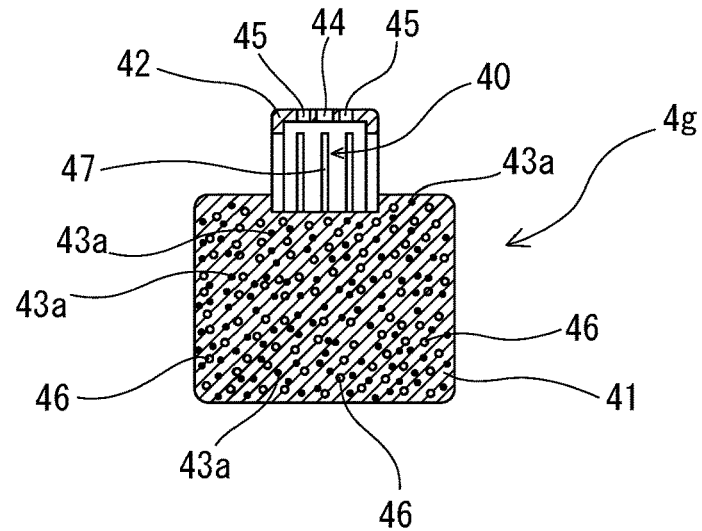
FIG. 11 is an enlarged vertical longitudinal sectional view of an embryo accommodation container of still another embodiment for use in the instrument of the present invention for fixedly transplanting the living body embryo into the uterus.
Figure 12:
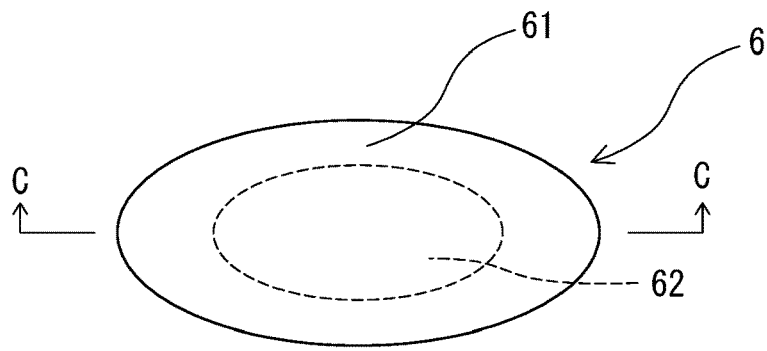
FIG. 12 is a plan view of a magnetic embryo accommodation container holding device for use in the instrument for fixedly transplanting the living body embryo into the uterus shown in FIG. 1.
Figure 13:
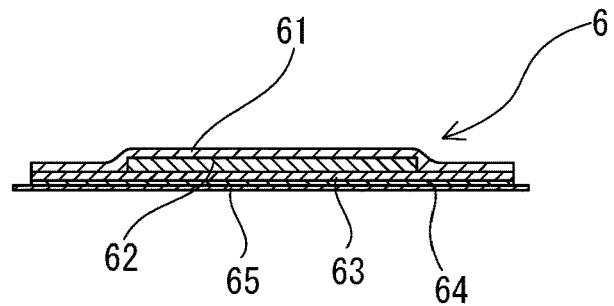
FIG. 13 is a sectional view taken along a C-C line of FIG. 12.

As with an embryo accommodation container 4g of an embodiment shown in FIG. 11, the embryo accommodation container may contain both a large number of bubbles 46 and a large number of minute magnetic materials 43a. The volume content rate at a part of the embryo accommodation container in which the minute magnetic particles are contained is preferably 0.1 to 5 vol % and especially preferably 0.5 to 3 vol %. The volume content rate at a part of the embryo accommodation container in which bubbles are contained is preferably 0.1 to 5 vol % and especially preferably 0.5 to 3 vol %. The sectional area of a bubble is favorably 0.0001 to 1.0 $mm^2$, more favorably 0.001 to 0.8 $mm^2$, and most favorably 0.01 to 0.3 $mm^2$. The embryo accommodation container 4g of this embodiment mixedly contains a large number of bubbles 46 and a large number of magnetic materials 43a. The way of the embryo accommodation container contains both the bubbles and the magnetic materials is not limited to the above-described way, but the embryo accommodation container may separately contain the bubbles and the magnetic materials.

In a case where the embryo accommodation container is formed of synthetic resin, it is possible to use any kind of resin, provided that the resin is capable of forming the embryo accommodation container. For example, it is possible to use synthetic rubber such as silicone rubber, urethane rubber, and butadiene rubber; natural rubber such as latex rubber; olefin elastomers (for example, polyethylene elastomer, polypropylene elastomer); amide elastomers (for example, polyamide elastomer); styrene elastomers (for example, styrene-butadiene-styrene copolymer, styrene-isoprene-styrene copolymer, styrene-ethylene butylene-styrene copolymer); thermoplastic elastomers such as thermoplastic polyurethane; and thermoplastic resin such as polyolefin (for example, polyethylene, polypropylene, ethylene-propylene copolymer), polyester (for example, polyethylene terephthalate, polybutylene terephthalate), and polyamide.

The container transfer tool 5 for transferring the embryo accommodation container 4 into the uterus is described below.

Figure 2:
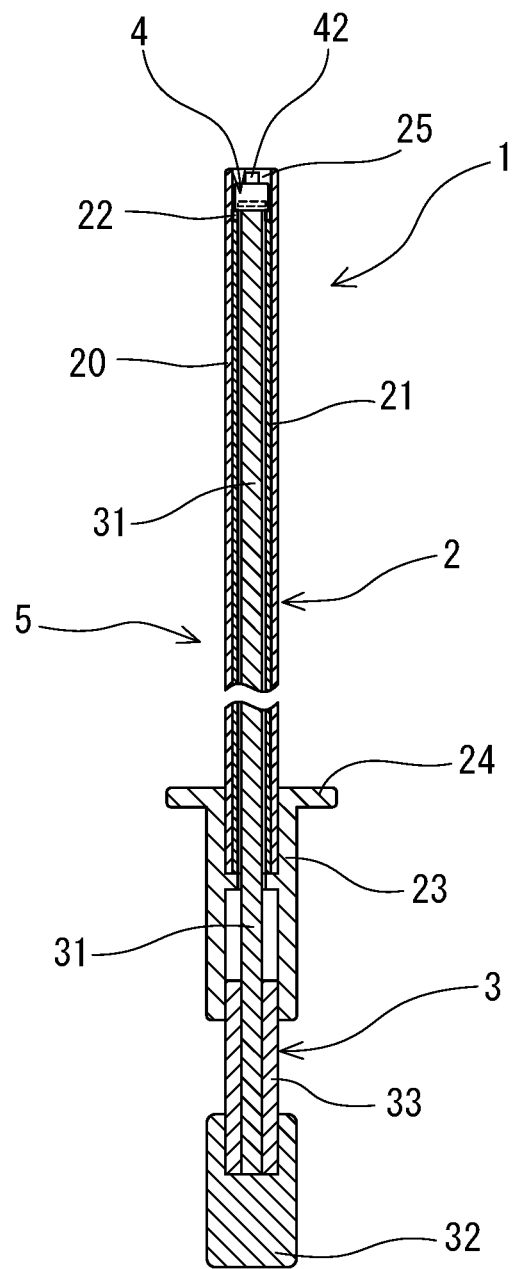
FIG. 2 is a partial vertical longitudinal sectional view of a living body embryo transplanting device into the uterus for use in the instrument for fixedly transplanting the living body embryo into the uterus shown in FIG. 1.

The container transfer tool 5 shown in FIGS. 1 and 2 has a flexible sheath 2 and a flexible shaft 3 slidably inserted into the flexible sheath.

In the container transfer tool 5 of this embodiment, the flexible sheath 2 has a container accommodation part 25 for accommodating the embryo accommodation container 4 at its distal end portion. In addition, the flexible sheath has a flexible outer tube 20 and a flexible inner tube 21 disposed inside the flexible outer tube 20. A distal end of the flexible inner tube 21 is positioned proximally from the distal end of the flexible outer tube 20 by a predetermined length. Inside the distal end portion of the flexible outer tube 20, a permanent magnet 22 for attracting the magnetic material 43 of the embryo accommodation container 4 thereto is disposed. In the container transfer tool 5 of this embodiment, the ring-shaped permanent magnet 22 is inserted into and fixed to the distal end portion of the outer tube 20 in such a way that the permanent magnet contacts a distal end surface of the inner tube 21. The container accommodation part 25 is formed between a distal end of the permanent magnet 22 and the distal end of the outer tube 20. As the permanent magnet, the ferrite magnet, the neodymium magnet, the platinum magnet, the alnico magnet, and the samarium cobalt magnet are preferable.

It is effective to provide the flexible sheath with the inner tube 21 to retain the position of the permanent magnet 22. But the flexible sheath does not necessarily have to be provided with the inner tube 21. A sheath hub 23 is fixed to a proximal end of the outer tube 20. The sheath hub 23 has a gripping part 24.

It is preferable that materials for forming the flexible sheath 2 (outer tube 20, inner tube 21) have flexibility and shape retainability to some extent. As the materials for forming the flexible sheath, it is possible to use polyester, polyolefin (for example, polyethylene, polypropylene, ethylene-propylene copolymer), polyamide (for example, nylon 6, nylon 66), polyester (for example, polyethylene terephthalate), and fluororesin (for example, PTFE, ETFE).

The flexible shaft 3 has a shaft body 31 and a shaft hub 32 provided at its proximal end. In the case of the flexible shaft 3 of this embodiment, the shaft hub 32 has a cylindrical part 33 projecting toward a distal end of the shaft 3. The cylindrical part 33 is fixed to the proximal end of the shaft body 31. Thus, the shaft body 31 is fixed to the hub 32 by means of the cylindrical part 33. The cylindrical part 33 of the shaft hub 32 is slidable inside the sheath hub 23. The cylindrical part 33 of the shaft hub 32 and the sheath hub 23 have sliding resistance to some extent. Unless both are moved relatively to each other, it is possible to hold the state between both (for example, the state shown in FIG. 2). The container transfer tool 5 may have the state shown in FIG. 2. More specifically, the container transfer tool may have a position holding function of maintaining a state in which the embryo accommodation container is accommodated inside the distal end of the sheath with the distal end portion of the shaft 3 in contact with the embryo accommodation container 4 or in close proximity thereto. In the container transfer tool of this embodiment, the position holding function is formed by the sliding resistance of a contact part of the shaft hub 32 (cylindrical part 33) which has penetrated into the sheath hub 23.

It is preferable that materials for forming the shaft body 31 have flexibility and shape retainability to some extent. As the materials for forming the shaft body, it is possible to use polyester, polyolefin (for example, polyethylene, polypropylene, ethylene-propylene copolymer), polyamide (for example, nylon 6, nylon 66), polyester (for example, polyethylene terephthalate), and fluororesin (for example, PTFE, ETFE). The shaft body 31 may have a core made of metal (for example, iron, stainless steel) or hard resin.

Figure 14:
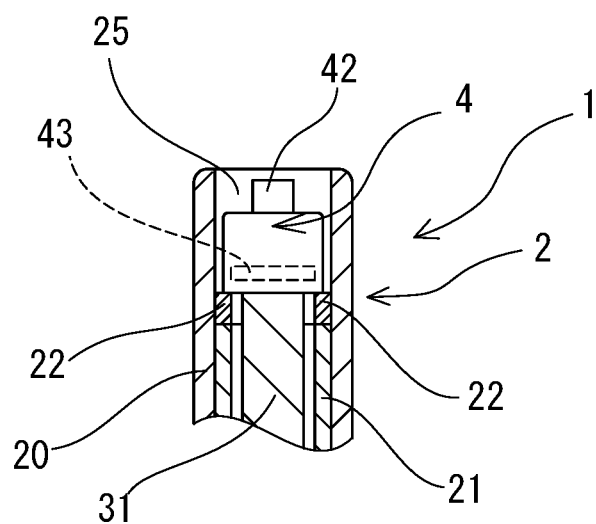
FIG. 14 is a distal end portion-enlarged view of the living body embryo transplanting device shown in FIG. 2.

In the container transfer tool 5 of this embodiment, as shown in FIG. 14, the embryo accommodation container 4 is accommodated inside the container accommodation part 25 with the embryo accommodation part 42 being located at the distal end side of the embryo accommodation container 4. Thus, a rear end surface of the embryo accommodation container 4 (rear end surface of body part 41) is directed toward the distal end of the shaft body 31. In this type of the container transfer tool, it is preferable that the magnetic material 43 provided inside the embryo accommodation container 4 is positioned at the proximal end side of the embryo accommodation container 4. Thereby it is possible to achieve a favorable magnetic coupling between the magnetic material 43 of the embryo accommodation container 4 and the ring-shaped permanent magnet 22.

Figure 15:
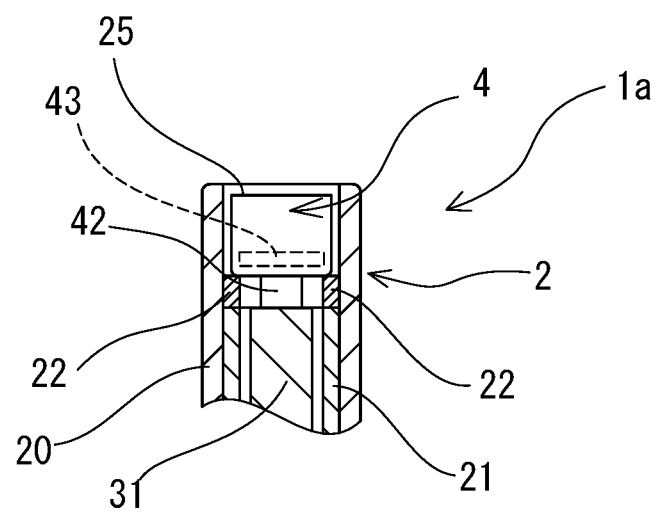
FIG. 15 is an enlarged partial vertical longitudinal sectional view of a living body embryo transplanting device of still another embodiment, which is used for the instrument of the present invention for fixedly transplanting the living body embryo into the uterus.

The form of accommodating the embryo accommodation container 4 inside the container accommodation part 25 is not limited to the above-described one. For example, as with a living body embryo transplanting device 1a into a uterus of an embodiment shown in FIG. 15, the embryo accommodation container 4 may be accommodated inside the container accommodation part 25 of the container transfer tool 5 with the embryo accommodation part 42 being located at the proximal end side of the embryo accommodation container. In this embodiment, the distal end surface of the embryo accommodation part 42 of the embryo accommodation container 4 is directed toward the distal end surface of the shaft body 31. In this type of the container transfer tool, it is preferable that the magnetic material 43 provided inside the embryo accommodation container 4 is positioned at the distal end side of the body part 41 of the embryo accommodation container 4. Thereby it is possible to achieve a favorable magnetic coupling between the magnetic material 43 of the embryo accommodation container 4 and the ring-shaped permanent magnet 22.

The magnetic embryo accommodation container holding device 6 is attached to the living body. The magnetic embryo accommodation container holding device 6 shown in the drawings has a lower sheet 63 forming the attaching part 63 and an upper surface portion (upper sheet) 61 pasted to an upper surface of the lower sheet 63 and to an upper surface of the magnet 62 in such a way as to wrap the magnet 62 fixed to the upper surface of the lower sheet 63.

As the lower sheet 63 and the upper sheet 61, it is possible to use a flexible synthetic resin sheet and various kinds of fabrics such as woven or nonwoven cloths formed from synthetic fiber and natural fiber. It is preferable that the lower sheet 63 and the upper sheet 61 are air-permeable. It is possible to impart air permeability to the lower sheet 63 and the upper sheet 61 by using air-permeable materials therefor and by forming a large number of pores through the lower sheet 63 and the upper sheet 61.

As the lower sheet 63 and the upper sheet 61, it is possible to utilize natural fibers such as bast fibers such as paper, cotton, *cannabis*, and jute; cellulose fibers such as vein fibers, for example, Mania hemp; animal fibers such as wool; silk fibers and protein fibers such as feather fibers; regenerated fibers such as regenerated cellulose fibers, for example, rayon, cupra fibers and regenerated fibers such as regenerated protein fibers; semi-synthetic fibers such as cellulose acetate fibers and promix fibers; nylon aramid fibers, polyethylene terephthalate fibers, polyester fibers, acrylic fibers, polyolefin fibers such as polyethylene and polypropylene; polyvinyl alcohol fibers; polyvinyl chloride fibers; polyvinylidene chloride fibers; polyvinyl chloride-based fibers; polyurethane fibers; polyoxymethylene fibers; polytetrafluoroethylene fibers; poly(p-phenylenebenzobis-chiazole)(PBT) fibers; and polyimide fibers.

As the magnet 62, permanent magnets are preferable. Permanent magnets having a sufficiently high magnetic force are suitable. A neodymium magnet, a platinum magnet, an alnico magnet, and a samarium cobalt magnet are preferable. It is preferable that the magnet 62 is thin. It is preferable that the magnet 62 is rectangular, elliptic or circular. It is especially preferable that the magnet is elliptic or formed as a corner-chamfered rectangle. The magnet 62 may be composed of a battery and an electromagnet. It is possible to use any kind of electromagnets so long as it is capable of generating a sufficiently high magnetic attractive force. A DC electromagnet is especially suitable. It is preferable that the electromagnet and the battery are thin.

In the magnetic embryo accommodation container holding device 6 of this embodiment, an adhesive surface 64 to be pasted to skin is formed on a lower surface of the lower sheet 63. Thereby the lower sheet can be easily pasted to an arbitrary portion of the skin. Thus, a pasted state can be maintained. As materials for forming the adhesive surface, known materials can be used. Examples of materials include plant-based materials such as guar gum, locust bean gum, carrageenan, alginic acid, sodium alginate, agar, gum arabic, gum tragacanth, karaya gum, pectin, and starch; microbial materials such as xanthan gum and acacia gum; animal-based natural polymers such as gelatin and collagen; celluloses such as methyl cellulose, ethyl cellulose, hydroxyethyl cellulose, and carboxymethylcellulose sodium; starch-based semi-synthetic polymers such as soluble starch, carboxymethyl starch, and dialdehyde starch; vinyl-based materials such as polyvinyl alcohol, polyvinyl pyrrolidone, and polyvinyl methacrylate; acrylic materials such as polyacrylic acid and sodium polyacrylate; and water-soluble polymers such as synthetic polymers, for example, polyethylene oxide and methyl vinyl ether/maleic anhydride copolymer.

In the magnetic embryo accommodation container holding device 6 of this embodiment, a release sheet 65 is pasted to a lower surface of the adhesive surface 64. The release sheet 65 is peeled off the lower surface of the adhesive surface 64 when the magnetic embryo accommodation container holding device 6 is used.

As the release sheet, sheets made of known materials can be used. Examples of the release sheet include films or sheets made of synthetic resin such as unstretched or stretched polypropylene, polyethylene terephthalate, polyethylene, polyvinyl chloride, polyester, polyvinylidene chloride, and polystyrene or silicone processed paper.

It is possible to use the magnetic embryo accommodation container holding device 6 which does not have the adhesive surface, but is attached to the living body by means of a fixture such as a belt.

The action of the instrument 10 of the present invention for fixedly transplanting the living body embryo into the uterus is described below with reference to the embodiment shown in FIGS. 1, 2, and 14.

An embryo (quadrant embryo, eight-split embryo, morula or blastocyst) which has been obtained by in-vitro fertilization and has grown in a predetermined period of time is prepared. The prepared embryo is inserted into the embryo accommodation part 42 from the embryo insertion portion 44 of the embryo accommodation container 4. Thereafter the embryo-accommodated embryo accommodation container 4 is immersed in a predetermined holding liquid (culture liquid).

Figure 23:
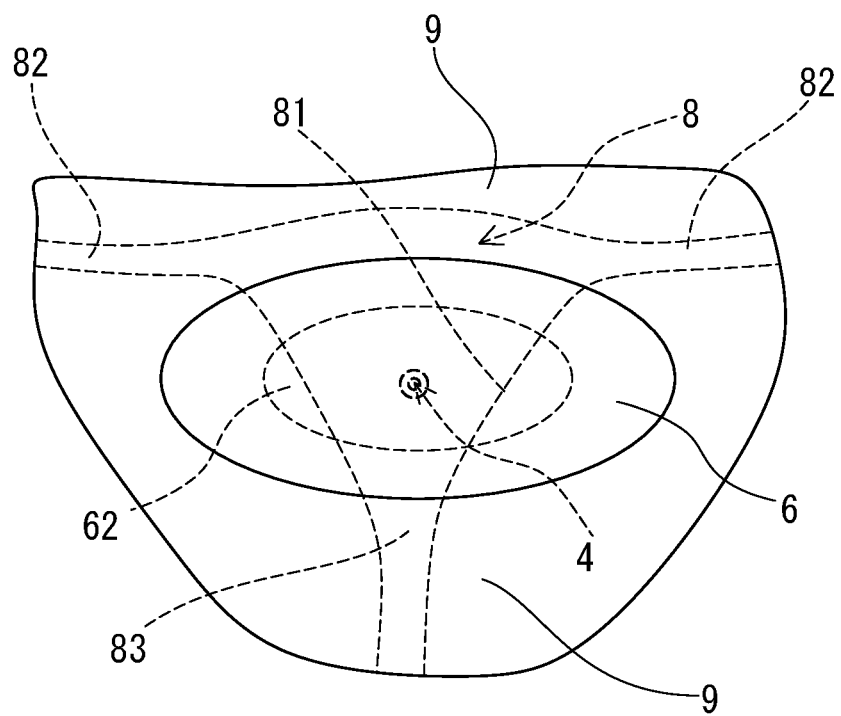
FIG. 23 is an explanatory view for explaining the action of the instrument of the present invention for fixedly transplanting the living body embryo into the uterus.

By using transabdominal or transvaginal ultrasonography, the position of a body surface corresponding to the target location inside a uterus 8 where an embryo is to be fixedly transferred is checked. As the location where the embryo is to be fixedly transferred, a preferable location is positioned above a uterus mouth 83 shown in FIG. 23, below an oviduct 82, and in the vicinity of a central portion in a vertical direction inside the uterus. Thereafter as shown in FIG. 23, the magnetic embryo accommodation container holding device 6 is fixed (more specifically, pasted) to the location of the body surface of a living body 9 corresponding to the central portion of the uterus which has been checked and confirmed.

Thereafter the embryo accommodation container 4 accommodating the embryo is accommodated inside the container accommodation part 25 of the container transfer tool 5. The embryo accommodation container 4 keeps the state of being accommodated inside the container accommodation part 25 with the magnetic material 43 of the embryo accommodation container being attracted by the permanent magnet 22 of the container transfer tool 5. Thereafter the container transfer tool 5 prepared in this manner is transvaginally inserted into the living body, and the distal end portion (embryo accommodation container 4) of the container transfer tool 5 is disposed at an appropriate portion 81 inside the uterus. As necessary, by using an ultrasonic inspection device or the like, the position of the embryo accommodation container is checked. Whether the container transfer tool 5 has reached the appropriate portion 81 inside the uterus may be checked by the attraction of the container transfer tool 5 to the permanent magnet 62 of the magnetic embryo accommodation container holding device 6.

By pulling the flexible sheath 2 toward the proximal end of the container transfer tool, with the flexible shaft 3 being held after the embryo accommodation container 4 reaches the appropriate portion 81 inside the uterus, the embryo accommodation container 4 contacts the distal end of the shaft body 31 and thereafter separates from the permanent magnet of the flexible sheath and also from the sheath.

Thereafter the embryo accommodation container 4 which has separated from the sheath is magnetically attracted by the permanent magnet 62 of the magnetic embryo accommodation container holding device 6 fixed (pasted) to the body surface and held at the appropriate portion inside the uterus. By pulling the container transfer tool 5 from which the embryo accommodation container 4 has separated out of the living body, the operation of fixedly transplanting the living body embryo into the uterus finishes. The embryo which has grown inside the embryo accommodation container 4 to such an extent that the embryo is capable of implanting on the endometrium escapes (in other words, moves out) from the embryo accommodation container 4 by itself and implants on the endometrium.

The form of the living body embryo transplanting device into the uterus, which is used for the instrument of the present invention for fixedly transplanting the living body embryo into the uterus is not limited to the above-described one.

Figure 16:
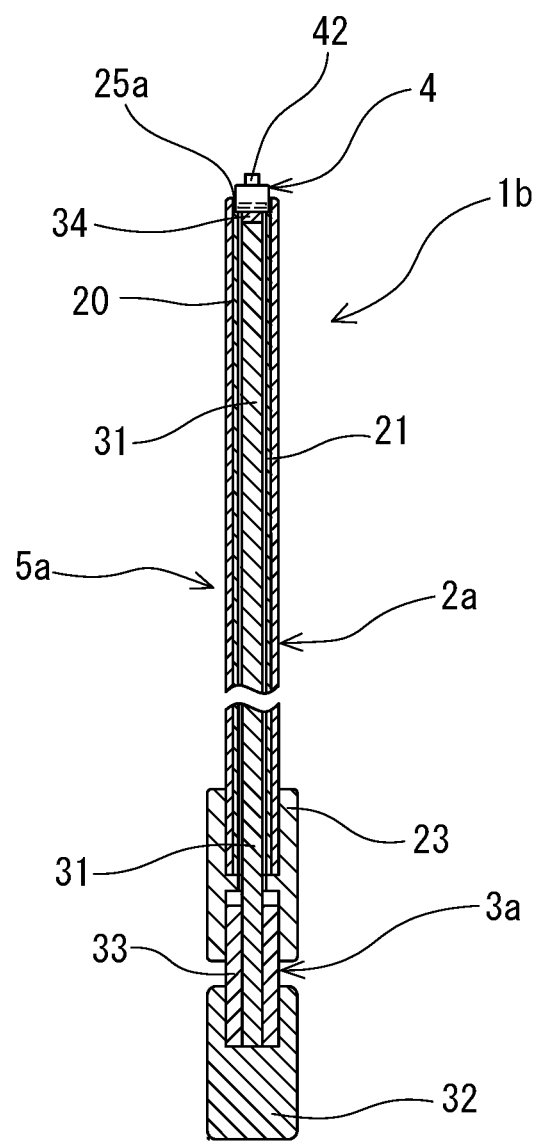
FIG. 16 is a vertical longitudinal sectional view of a living body embryo transplanting device of still another embodiment, which is used for the instrument of the present invention for fixedly transplanting the living body embryo into the uterus.

The living body embryo transplanting device into the uterus may be constructed as a living body embryo transplanting device 1b into the uterus as shown in FIG. 16. The basic construction of the living body embryo transplanting device 1b into the uterus is the same as that of the above-described living body embryo transplanting device 1. The living body embryo transplanting device 1b into the uterus has the embryo accommodation container 4 and a container transfer tool 5a holding the embryo accommodation container 4 at its distal end portion.

As the embryo accommodation container 4 for use in the living body embryo transplanting device 1b into the uterus, it is possible to use the embryo accommodation containers of all of the above-described embodiments.

The container transfer tool 5a has a flexible sheath 2a and a flexible shaft 3a slidably inserted into the flexible sheath.

In the container transfer tool 5a of this embodiment, the flexible sheath 2a has a container accommodation part 25a for accommodating the rear end portion of the embryo accommodation container 4 at the distal end portion of the flexible sheath. In addition, the flexible sheath has the flexible outer tube 20 and the flexible inner tube 21 disposed inside the flexible outer tube 20. The distal end of the flexible inner tube 21 is positioned proximally from the distal end of the flexible outer tube 20 by a predetermined length. It is effective to provide the flexible sheath with the inner tube 21 to form the container accommodation part 25a. But the flexible sheath does not necessarily have to be provided with the inner tube 21. The sheath hub 23 is fixed to the proximal end of the outer tube 20. The sheath hub 23 may have the gripping part as with the one shown in FIG. 2. As materials for forming the flexible sheath 2 (the outer tube 20, the inner tube 21), those described previously are used.

The flexible shaft 3a has the shaft body 31, a permanent magnet 34 fixed to the distal end of the shaft body 31, and the shaft hub 32 provided at the proximal end of the shaft body 31. As materials for forming the shaft body 31, those described previously are used. The flexible shaft 3a is provided with the permanent magnet 34 to attract the magnetic material 43 of the embryo accommodation container 4 thereto. As the permanent magnet, the ferrite magnet, the neodymium magnet, the platinum magnet, the alnico magnet, and the samarium cobalt magnet are preferable.

In the flexible shaft 3a of this embodiment, the shaft hub 32 also has the cylindrical part 33 projecting toward the distal end of the flexible shaft 3a. The cylindrical part 33 is fixed to the proximal end of the shaft body 31. Thus, the shaft body 31 is fixed to the hub 32 by means of the cylindrical part 33. The cylindrical part 33 of the shaft hub 32 is slidable inside the sheath hub 23. The cylindrical part 33 of the shaft hub 32 and the sheath hub 23 have sliding resistance to some extent. Unless both are moved relatively to each other, it is possible to hold the state between both (for example, the state shown in FIG. 16). The container transfer tool 5a may have the state shown in FIG. 16. More specifically, the container transfer tool 5a may have a position holding function of maintaining a state in which the rear end portion of the embryo accommodation container is accommodated inside the distal end of the sheath with the embryo accommodation container 4 being attractively held by the permanent magnet 34 of the shaft 3a. In the container transfer tool of this embodiment, the position holding function is formed by the sliding resistance of a contact part of the shaft hub 32 (cylindrical part 33) which has penetrated into the sheath hub 23.

In the container transfer tool 5a of this embodiment, as shown in FIG. 16, the embryo accommodation container 4 is accommodated inside the container accommodation part 25a with the embryo accommodation part 42 being located at the distal end side of the embryo accommodation container. Thus, the rear end surface of the embryo accommodation container 4 (rear end surface of the body part 41) is directed toward the distal end surface of the shaft body 31. The form of accommodating the embryo accommodation container 4 inside the container accommodation part 25a is not limited to the above-described one. For example, the embryo accommodation container 4 may be accommodated inside the container accommodation part 25*a* of the container transfer tool 5*a* with the embryo accommodation part 42 being located at the proximal end side of the embryo accommodation container.

Figure 17:
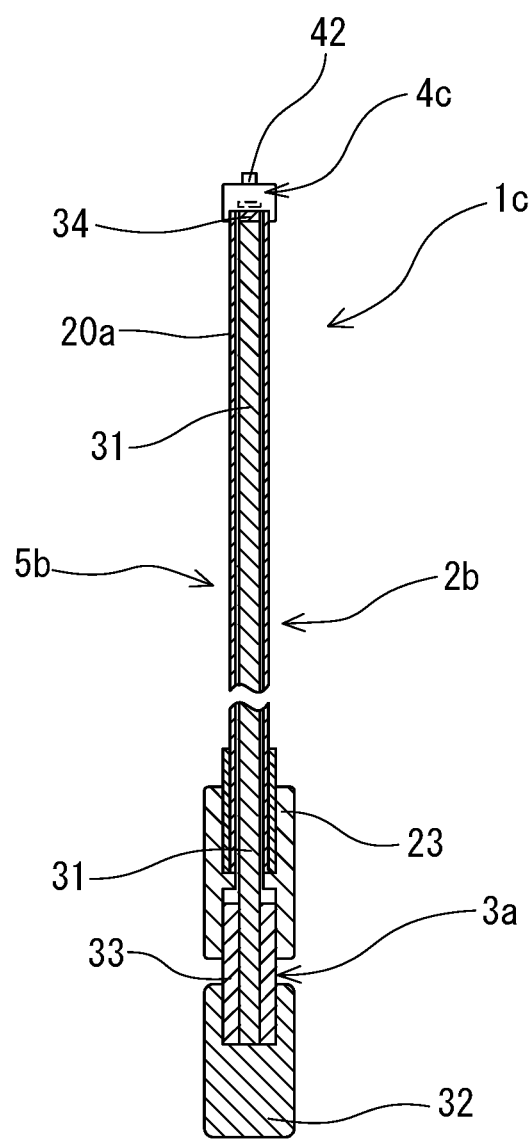
FIG. 17 is a vertical longitudinal sectional view of a living body embryo transplanting device of still another embodiment, which is used for the instrument of the present invention for fixedly transplanting the living body embryo into the uterus.

The living body embryo transplanting device into the uterus may be formed as a living body embryo transplanting device 1*c* into the uterus as shown in FIG. 17. The basic construction of the living body embryo transplanting device 1*c* into the uterus is the same as that of the above-described living body embryo transplanting device 1*b*. The living body embryo transplanting device 1*c* into the uterus has an embryo accommodation container 4*c* and a container transfer tool 5*b* for holding the embryo accommodation container 4*c* at the distal end portion of the container transfer tool.

The embryo accommodation container 4*c* for use in the living body embryo transplanting device 1*c* into the uterus has a sheath distal end insertion portion at the rear end portion of the embryo accommodation container. Except for this point, the construction of the embryo accommodation container 4*c* is the same as that of the above-described embryo accommodation container 4. It is possible to use the embryo accommodation containers of all the types of the above-described embodiments as the embryo accommodation container.

The container transfer tool 5*b* has a flexible sheath 2*b* and the flexible shaft 3*a* slidably inserted into the flexible sheath 2*b*.

In the container transfer tool 5*b* of this embodiment, a distal end portion of the flexible sheath 2*b* is capable of entering the rear end portion of the embryo accommodation container 4*c*. The flexible sheath 2*b* has a flexible outer tube 20*a*. The sheath hub 23 is fixed to a proximal end of the flexible outer tube 20*a*. As materials for forming the flexible sheath 2*b* (the outer tube 20*a*), those described previously are used.

The flexible shaft 3*a* has the shaft body 31, the permanent magnet 34 fixed to the distal end of the shaft body 31, and the shaft hub 32 provided at the proximal end of the shaft body 31. As materials for forming the shaft body 31, those described previously are used. The flexible shaft 3*a* is provided with the permanent magnet 34 to attract the magnetic material 43 of the embryo accommodation container 4*c* thereto. As the permanent magnet, the ferrite magnet, the neodymium magnet, the platinum magnet, the alnico magnet, and the samarium cobalt magnet are preferable.

In the flexible shaft 3*a* of this embodiment, the shaft hub 32 also has the cylindrical part 33 projecting toward the distal end of the flexible shaft 3*a*. The cylindrical part 33 is fixed to the proximal end of the shaft body 31. Thus, the shaft body 31 is fixed to the hub 32 by means of the cylindrical part 33. The cylindrical part 33 of the shaft hub 32 is slidable inside the sheath hub 23. The cylindrical part 33 of the shaft hub 32 and the sheath hub 23 have sliding resistance to some extent. Unless both are moved relatively to each other, both are capable of holding the state (for example, state shown in FIG. 17). The container transfer tool 5*b* may have the state shown in FIG. 17. More specifically, the container transfer tool 5*b* may have a position holding function of maintaining a state in which the rear end portion of the embryo accommodation container is accommodated inside the distal end of the sheath and the embryo accommodation container 4*c* is attractively held by the permanent magnet 34 of the shaft 3*a*. In the container transfer tool of this embodiment, the position holding function is formed by the sliding resistance of a contact part of the shaft hub 32 (cylindrical part 33) which has penetrated into the sheath hub 23.

In the container transfer tool 5*b* of this embodiment, as shown in FIG. 17, the embryo accommodation container 4*c* is mounted on the sheath 2*b* with the embryo accommodation part 42 being located at the distal end side of the embryo accommodation container. Thus, a rear end surface of the embryo accommodation container 4*c* (rear end surface of the body part 41) is directed toward the distal end surface of the shaft body 31. The form of mounting the embryo accommodation container 4*c* on the sheath 2*b* is not limited to the above-described one. For example, the embryo accommodation container 4*c* may be mounted on the distal end portion of the sheath 2*b* with the embryo accommodation part 42 of the embryo accommodation container 4*c* being located at the proximal end side of the embryo accommodation container.

Figure 18:
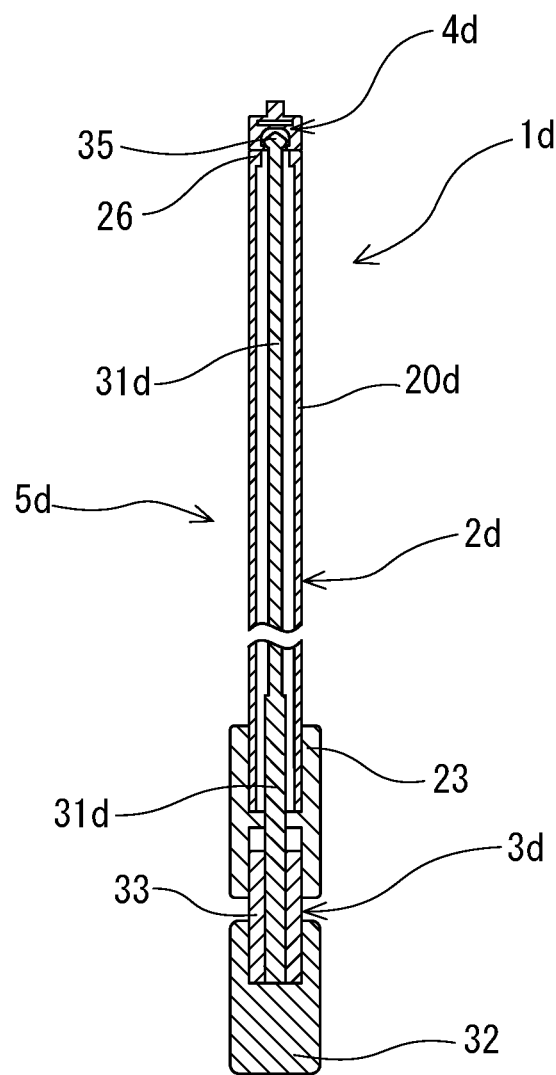
FIG. 18 is a vertical longitudinal sectional view of a living body embryo transplanting device of still another embodiment, which is used for the instrument of the present invention for fixedly transplanting the living body embryo into the uterus.
Figure 19:
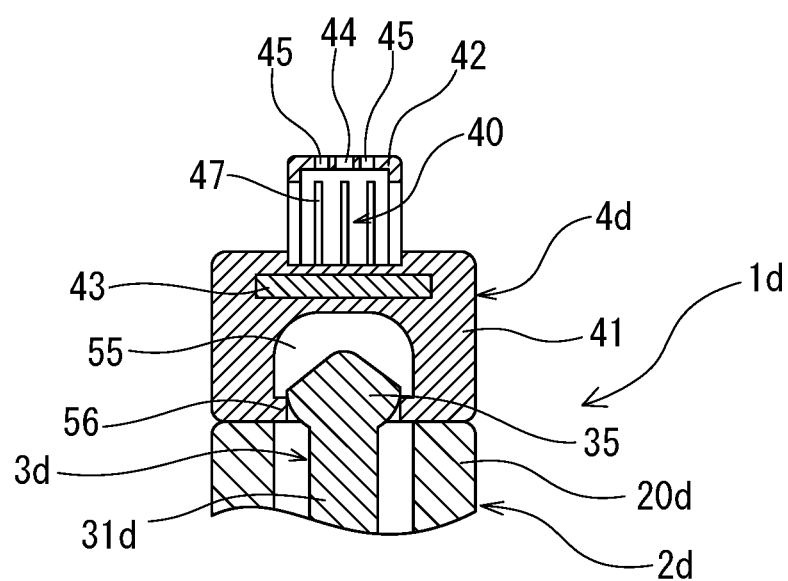
FIG. 19 is an enlarged view of a distal end portion of the living body embryo transplanting device shown in FIG. 18.

The living body embryo transplanting device into the uterus may be formed as a living body embryo transplanting device 1*d* into the uterus as shown in FIGS. 18 and 19. The basic construction of the living body embryo transplanting device 1*d* into the uterus is the same as that of the above-described living body embryo transplanting device 1. The living body embryo transplanting device 1*d* into the uterus has an embryo accommodation container 4*d* and a container transfer tool 5*d* for holding the embryo accommodation container 4*d* at the distal end portion of the container transfer tool.

The embryo accommodation container 4*d* for use in the living body embryo transplanting device 1*d* into the uterus has a shaft distal end mounting portion 55 at the rear end portion of the embryo accommodation container. As shown in FIG. 19, the shaft distal end mounting portion 55 provided at the rear end portion of the embryo accommodation container 4*d* has an accommodation portion for accommodating the distal end portion of the shaft and a small diameter portion 56 provided at an open portion of the accommodation portion. Except for this point, the construction of the embryo accommodation container 4*d* is the same as that of the above-described embryo accommodation container 4. As the embryo accommodation container, it is possible to use the embryo accommodation containers of all the types of the above-described embodiments.

The container transfer tool 5*d* has a flexible sheath 2*d* and a flexible shaft 3*d* slidably inserted into the flexible sheath 2*d*.

The flexible shaft 3*d* has a shaft body 31*d* and the shaft hub 32 provided at a proximal end of the shaft body 31*d*. As materials for forming the shaft body 31*d*, those described previously are used. The container transfer tool 5*d* of this embodiment is provided with a bulged portion 35 at a distal end of the shaft body 31*d* of the flexible shaft 3*d*. Upon pressing of the shaft 3*d* toward the shaft distal end mounting portion 55, the bulged portion 35 widens the small diameter portion 56 of the embryo accommodation container 4*d*, passes therethrough, and is capable of penetrating into the shaft distal end mounting portion 55. The bulged portion 35 which has penetrated into the shaft distal end mounting portion prevents the embryo accommodation container 4*d* from separating from a distal end portion of the shaft body 31*d*. In the instrument of this embodiment for transplanting the living body embryo into the uterus, the bulged portion 35 has a tapered distal end portion whose diameter decreases toward its distal end, a maximum diameter portion provided at a proximal end of the tapered distal end portion, and a proximal end diameter decreasing portion whose diameter decreases toward the proximal end of the bulged portion. An outer diameter of the maximum diameter portion is set a little larger than an inner diameter of an open portion of the small diameter portion 56 of the embryo accommodation container 4d. By pressing the tapered distal end portion of the bulged portion 35 against the small diameter portion 56 of the embryo accommodation container 4d and thereafter pressing the shaft 3d toward the shaft distal end mounting portion, the bulged portion 35 is capable of penetrating into the shaft distal end mounting portion 55 of the embryo accommodation container 4d.

The flexible sheath 2d has a flexible outer tube 20d. The sheath hub 23 is fixed to a proximal end of the outer tube 20d. As materials for forming the flexible sheath 2d (outer tube 20d), those described previously are used. In the container transfer tool 5d of this embodiment, a distal end portion of the outer tube 20d of the flexible sheath 2d is formed as a thick portion 26 which contacts a proximal end surface of the embryo accommodation container 4d. The thick portion 26 does not deform due to the contact.

In the flexible shaft 3d of this embodiment, the shaft hub 32 has the cylindrical part 33 projecting toward the distal end of the flexible shaft 3d. The cylindrical part 33 is fixed to the proximal end of the shaft body 31. Thus, the shaft body 31 is fixed to the hub 32 by means of the cylindrical part 33. The cylindrical part 33 of the shaft hub 32 is slidable inside the sheath hub 23. The cylindrical part 33 of the shaft hub 32 and the sheath hub 23 have sliding resistance to some extent. Unless both are moved relatively to each other, it is possible to hold a state in which as shown in FIG. 19, the embryo accommodation container 4d is mounted on a distal end portion of the shaft body 31d and the proximal end surface of the embryo accommodation container 4d is in contact with a distal end surface of the sheath 2d. In other words, the container transfer tool 5d has a position holding function of holding the state of the embryo accommodation container shown in FIG. 19. In the container transfer tool of this embodiment, the position holding function is formed by the sliding resistance of a contact part of the shaft hub 32 (cylindrical part 33) which has penetrated into the sheath hub 23.

In the container transfer tool 5d of this embodiment, as shown in FIG. 19, the embryo accommodation container 4d is mounted on the shaft 3d with the embryo accommodation part 42 being located at the distal end side of the embryo accommodation container 5d. Thus, a rear end surface of the embryo accommodation container 4d (rear end surface of the body part 41) is directed toward the distal end of the shaft body 31d.

In the container transfer tool 5d of this embodiment, by pulling the shaft 3d toward the proximal end of the instrument for transplanting the living body embryo into the uterus, with the shaft being held inside the sheath hub 23 in a state shown in FIG. 19, the bulged portion 35 of the shaft body 31d separates from the shaft distal end mounting portion 55 of the embryo accommodation container 4d. Thereby the embryo accommodation container 4d separates from the container transfer tool 5d.

A living body embryo transplanting device 1e into the uterus, which is used for the instrument of the present invention, shown in FIGS. 20 through 22, for fixedly transplanting the living body embryo into the uterus is described below.

Figure 20:
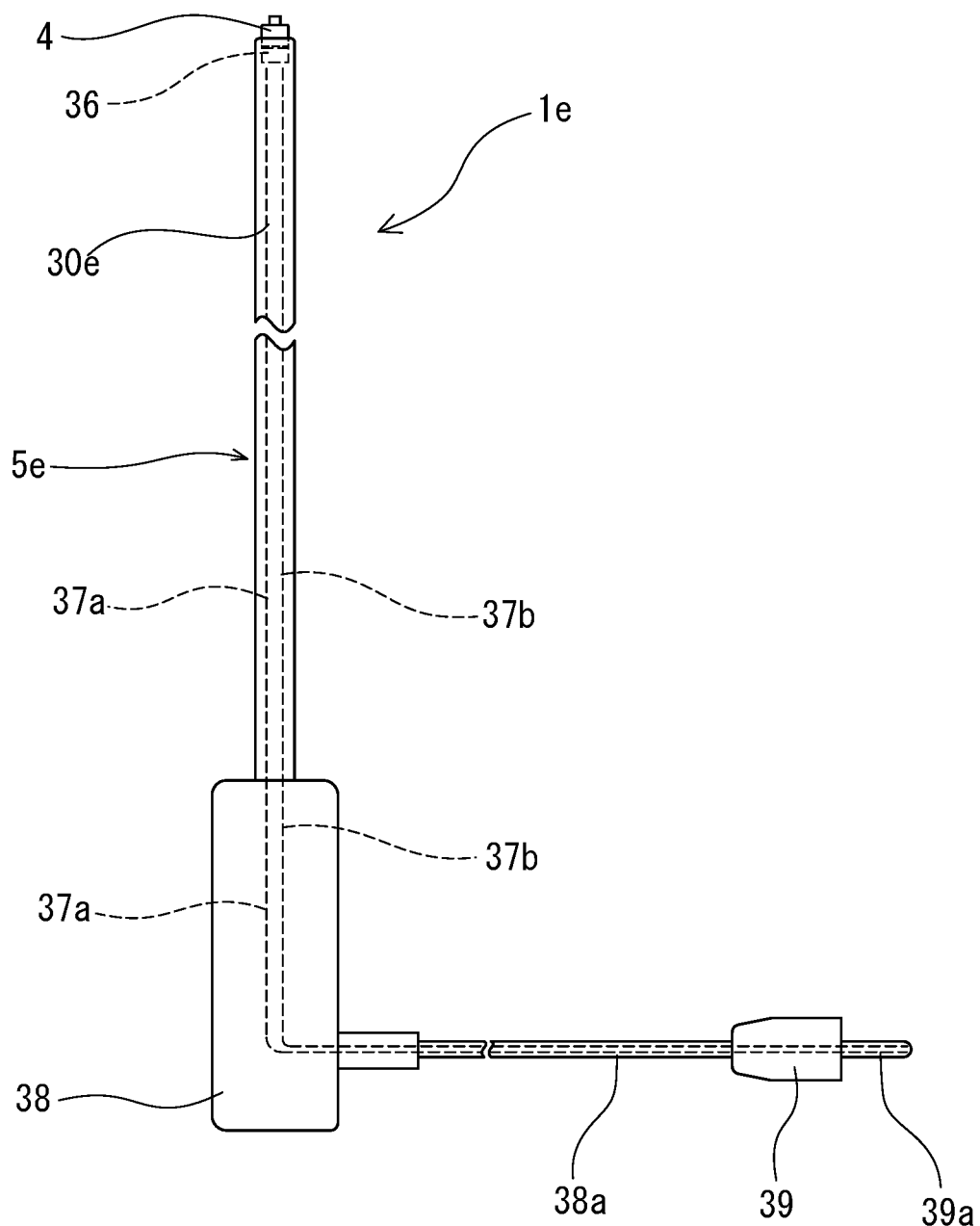
FIG. 20 is an outlook view of a living body embryo transplanting device of still another embodiment, which is used for the instrument of the present invention for fixedly transplanting the living body embryo into the uterus.

FIG. 20 is an outlook view of a living body embryo transplanting device of another embodiment for use in the instrument of the present invention for fixedly transplanting the living body embryo into the uterus. FIG. 21 is a block diagram of an electromagnet control part for use in the living body embryo transplanting device shown in FIG. 20. FIG. 22 is an enlarged view of a distal end portion of the living body embryo transplanting device shown in FIG. 20.

The living body embryo transplanting device 1e into the uterus has the embryo accommodation container 4, a container transfer tool 5e for transferring the embryo accommodation container with the container transfer tool 5e holding the embryo accommodation container at its distal end portion, and a power supply part (controller) 50 for supplying an electric power to an electromagnet of the container transfer tool 5e. The embryo accommodation container 4 is the same as the above-described embryo accommodation container 4. As the embryo accommodation container 4, it is possible to use the embryo accommodation containers, having the magnetic material, of all the types of the embryo accommodation containers described previously in the embodiments.

Figure 22:
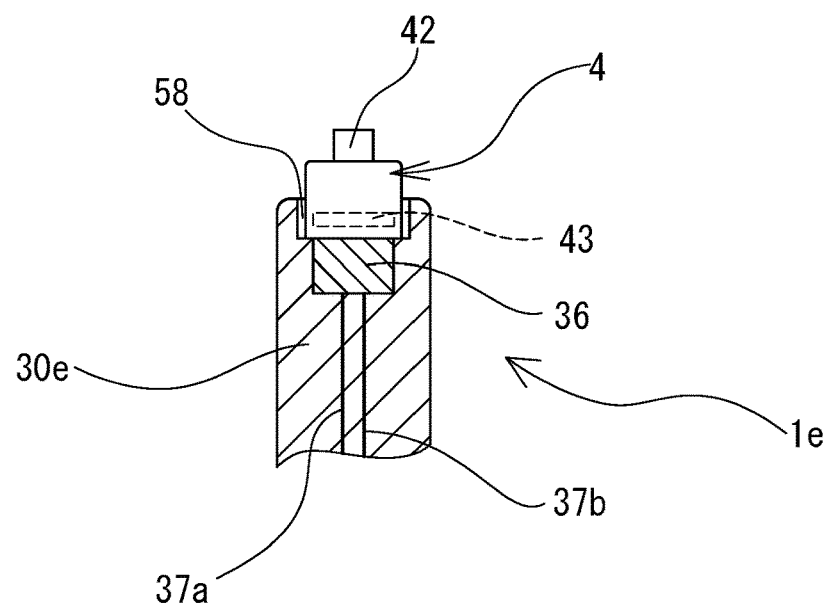
FIG. 22 is a partly enlarged sectional view of a distal end portion of the living body embryo transplanting device shown in FIG. 20.

The container transfer tool 5e shown in FIGS. 20 and 22 has a flexible shaft 30e and an electromagnet 36 disposed at a distal end portion of the flexible shaft 30e. In the container transfer tool 5e of this embodiment, as shown in FIG. 22, the flexible shaft 30e has a container accommodation part 58 for accommodating a rear end portion of the embryo accommodation container 4 at the distal end portion of the flexible shaft 30e. The container transfer tool 5e has the electromagnet 36 disposed inside the distal end portion of the flexible shaft 30e, more specifically, at a position a little proximal from the distal end of the flexible shaft 30e. The electromagnet 36 forms a bottom surface portion of the container accommodation part 58 or is positioned in the vicinity of the bottom surface portion of the container accommodation part 58. Upon energization, the electromagnet 36 magnetically attracts the magnetic material 43 of the embryo accommodation container 4, thereby holding the embryo accommodation container 4 at the distal end portion of the container transfer tool 5e. Conductor wires 37a, 37b are connected to the electromagnet 36.

It is possible to use any types of electromagnets so long as they are small and capable of generating a sufficiently high magnetic attractive force. A DC electromagnet is especially suitable as the electromagnet.

The flexible shaft 30e is solid. The flexible shaft 30e may be hollow. It is preferable that materials for forming the flexible shaft 30e have flexibility and shape retainability to some extent. As the materials for forming the flexible shaft, it is possible to use polyester, polyolefin (for example, polyethylene, polypropylene, ethylene-propylene copolymer), polyamide (for example, nylon 6, nylon 66), polyester (for example, polyethylene terephthalate), and fluororesin (for example, PTFE, ETFE). The flexible shaft 30e may have a core material made of a metal (for example, iron, stainless steel) or hard resin.

The flexible shaft 30e is provided with a shaft hub 38 at its rear end. The shaft hub 38 is provided with a cable 38a. The cable 38a is provided with a connector 39 at an end portion thereof. The conductor wires 37a, 37b penetrate the shaft 30e and are extended to a terminal 39a provided at a rear end of the 38a cable through the shaft hub, the cable, and the connector.

The controller 50 which is the power supply part supplies an electric power to the electromagnet 36 of the container transfer tool 5e to generate magnetism. The controller 50 of this embodiment has a construction as shown in FIG. 21. More specifically, the controller 50 has a connector attaching part which receives the terminal 39a of the container transfer tool 5e and on which the connector 39 can be mounted. The controller has an electric power supply circuit for supplying the electric power to the electromagnet of the container transfer tool 5e from the terminal 39a of the container transfer tool 5e mounted on the connector attaching part.

Figure 21:
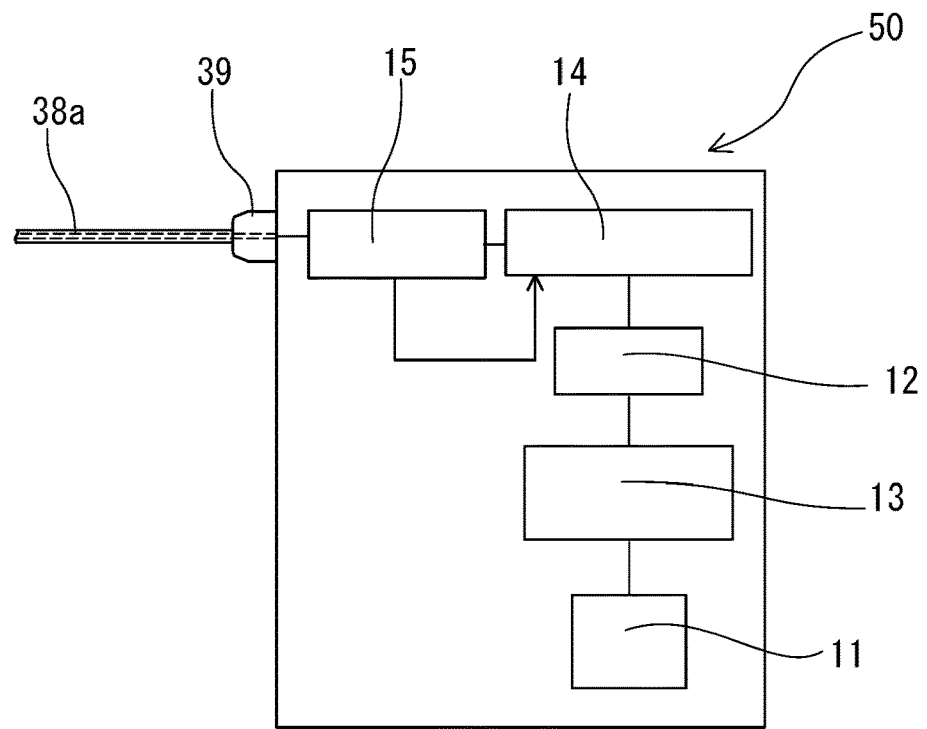
FIG. 21 is a block diagram of an electromagnet control part for use in the living body embryo transplanting device shown in FIG. 20.

In this embodiment, as shown in FIG. 21, the electric power supply circuit has a power supply portion 11, a power switch 12, and an electromagnetic force adjustment portion 14. As the power supply portion 11, a DC power supply is preferable. A constant-voltage DC power supply is especially preferable. As the electromagnetic force adjustment portion 14, an adjustable resistor for manually adjusting a power supply amount, more specifically, a supply current amount is used. The controller 50 of this embodiment has a current detection portion 15 which may automatically adjust the electromagnetic force adjustment portion 14 by using a detected electric current value. The controller 50 of this embodiment has a polarity conversion switch 13. The polarity conversion switch 13 is provided to convert the polarity of the DC power supply. In a case where the embryo accommodation container 4 is attracted to the container transfer tool 5e due to residual magnetism of the electromagnet, by changing over the polarity conversion switch 13 before turning off the power switch, the electromagnet generates a repulsive magnetism. Thereby it is possible to allow the embryo accommodation container 4 to escape securely from the container transfer tool 5e.

An embryo accommodation container collection instrument for use in the instrument of the present invention for fixedly transplanting the living body embryo into the uterus is described below.

Figure 24:
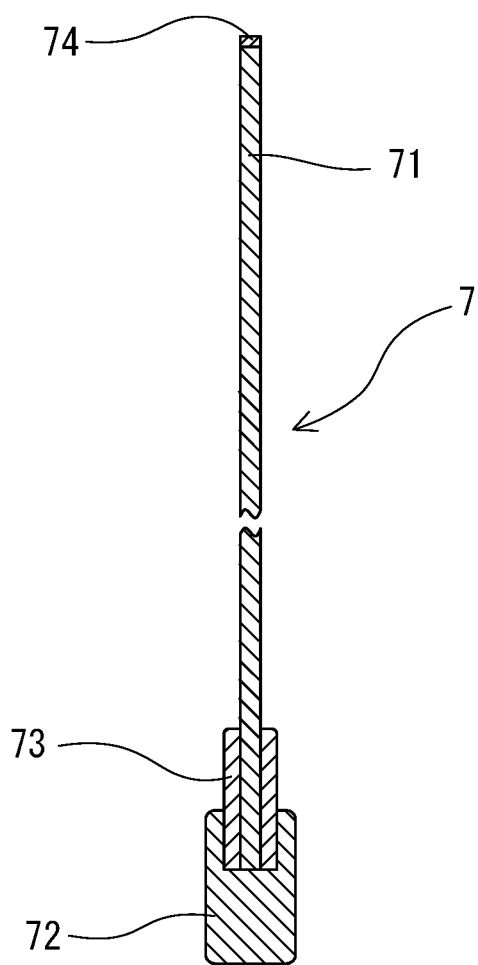
FIG. 24 is a vertical longitudinal sectional view showing one example of the embryo accommodation container collection instrument for use in the instrument of the present invention for fixedly transplanting the living body embryo into the uterus.

FIG. 24 is a vertical longitudinal sectional view showing one example of the embryo accommodation container collection instrument for use in the instrument of the present invention for fixedly transplanting the living body embryo into the uterus. An embryo accommodation container collection instrument 7 of this embodiment has a flexible shaft 71, a permanent magnet 74 fixed to a distal end of the shaft 71, and a shaft hub 72 provided at a proximal end of the shaft 71. The shaft hub 72 has a tubular proximal end portion reinforcing part 73. It is preferable that materials for forming the shaft 71 have flexibility and shape retainability to some extent. As the materials for forming the shaft 71, it is possible to use polyester, polyolefin (for example, polyethylene, polypropylene, ethylene-propylene copolymer), polyamide (for example, nylon 6, nylon 66), polyester (for example, polyethylene terephthalate), and fluororesin (for example, PTFE, ETFE). The flexible shaft 71 may have a core material made of a metal (for example, iron, stainless steel) or hard resin.

The shaft 71 is provided with the permanent magnet 74 to attract the magnetic material 43 of the embryo accommodation container 4 thereto. As the permanent magnet, the ferrite magnet, the neodymium magnet, the platinum magnet, the alnico magnet, and the samarium cobalt magnet are preferable.

The embryo accommodation container collection instrument 7 of this embodiment is substantially the same as the flexible shaft 3a of the above-described living body embryo transplanting device 1b into the uterus. For the embryo accommodation container collection instrument 7, it is possible to use the flexible sheath 2, of the above-described container transfer tool, having the magnet 22, the above-described flexible shaft 3a having the magnet at its distal end, and the above-described container transfer tool 5e having the electromagnet, and the controller 50.

Figure 25:
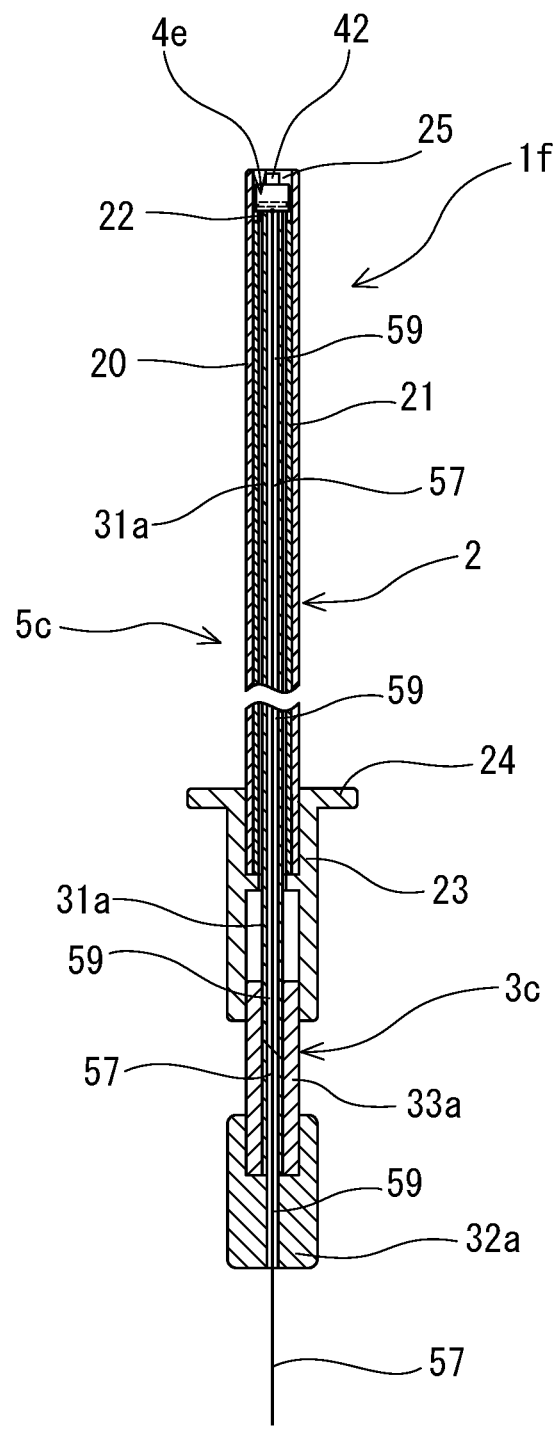
FIG. 25 is a vertical longitudinal sectional view of a living body embryo transplanting device of still another embodiment, which is used for the instrument of the present invention for fixedly transplanting the living body embryo into the uterus.
Figure 26:
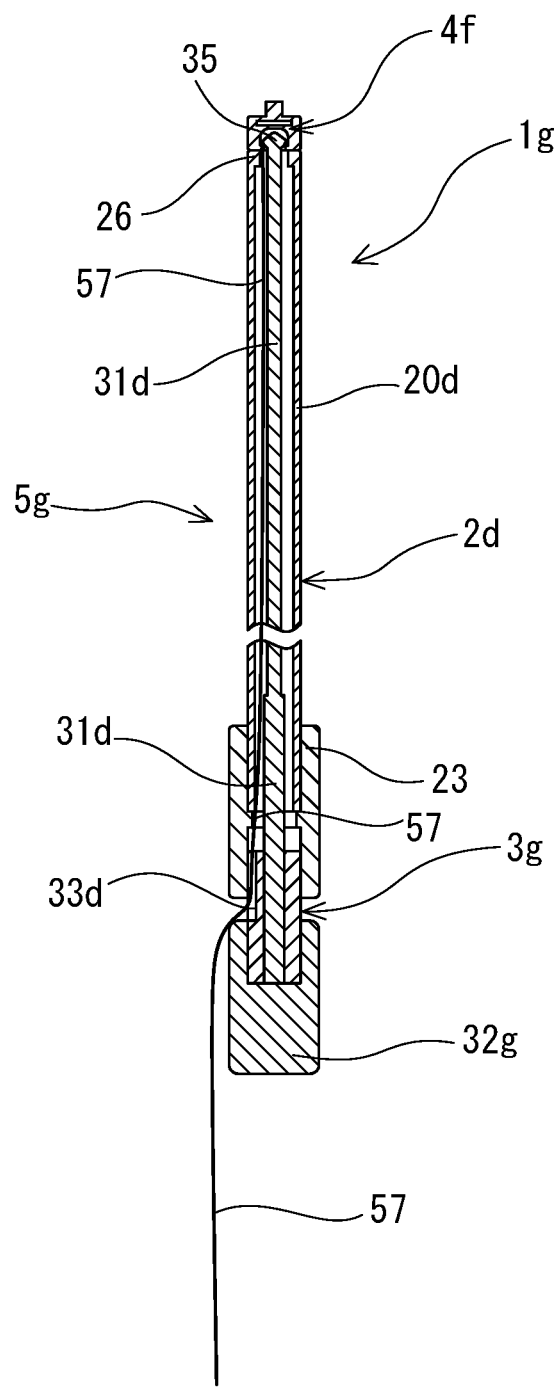
FIG. 26 is a vertical longitudinal sectional view of a living body embryo transplanting device of still another embodiment, which is used for the instrument of the present invention for fixedly transplanting the living body embryo into the uterus.

As with living body embryo transplanting devices 1f and 1g of embodiments shown respectively in FIGS. 25 and 26, the devise of all of the above-described embodiments for fixedly transplanting the living body embryo into the uterus may have a linear member 57 for collection whose one end is fixed to the embryo accommodation container and whose other end is extended toward the rear end of the shaft-shaped container transfer tool.

The living body embryo transplanting devices 1f and 1g of the embodiments shown respectively in FIGS. 25 and 26 have the linear member 57 for collection whose one end is fixed to the embryo accommodation container and whose other end is extended toward the rear end of the shaft-shaped container transfer tool. The other end portion of each linear member 57 is extended to the outside of the instruments for fixedly transplanting the living body embryo into the uterus from a proximal end portion of a linear member insertion part 59.

Figure 27:
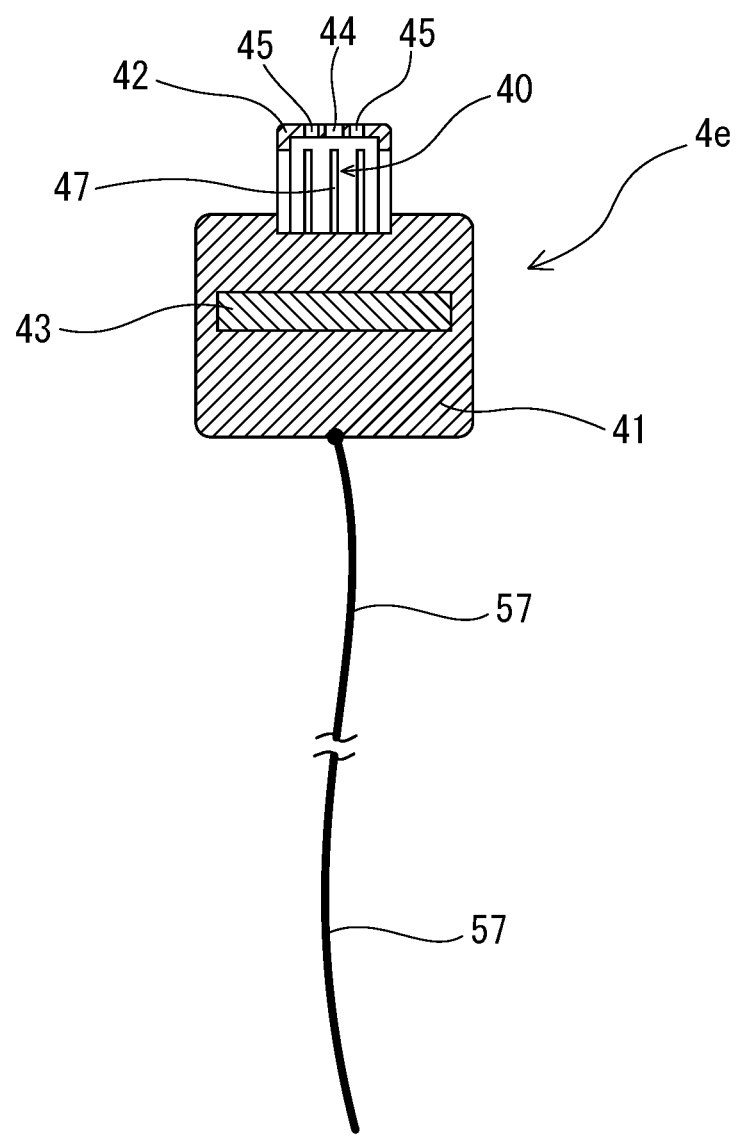
FIG. 27 is an enlarged vertical longitudinal sectional view of an embryo accommodation container of still another embodiment for use in the instrument of the present invention for fixedly transplanting the living body embryo into the uterus.

As the embryo accommodation container for use in the living body embryo transplanting device 1f of this embodiment into the uterus, an embryo accommodation container 4e as shown in FIG. 27 is used. The embryo accommodation container 4e has the linear member 57 for collection whose one end is fixed to the embryo accommodation container. As the embryo transplantation container, it is possible to use the embryo transplantation containers of all of the above-described types. In the embryo accommodation container 4e of this embodiment, one end of the linear member 57 for collection is fixed to a lower surface of the body part 41 of the embryo accommodation container 4e. The embryo accommodation containers of all of the above-described embodiments and all of embodiments to be described later may have the linear member 57 for collection whose one end is fixed to the embryo accommodation container.

It is preferable that the linear member 57 for collection has a predetermined length and the other end portion of the linear member 57 for collection extends from the living body in a state in which the container transfer tool has been pulled out of the living body after the embryo accommodation container 4e is disposed at the target portion of the living body (more specifically, inside uterus). The linear member 57 for collection which has a tensile strength to some extent and is flexible is suitable. As the linear member 57 for collection, it is possible to use a thread, a thin metal wire, and a stranded thread, and a stranded thin metal wire. As the thread, it is possible to use a thread of a synthetic fiber or a thread of a natural fiber, a mixture of the synthetic fiber and the natural fiber, and a stranded thread of them. As the synthetic fiber, it is possible to use organic synthetic fibers (for example, polyester, polyamide, polyolefin, carbon fiber) and inorganic synthetic fibers (for example, glass fiber, ceramic fiber). It is possible to use any kind of the thin metal wire. For example, it is possible to use a stainless-steel thin wire, a super-elastic metal thin wire, an amorphous metal thin wire, and stranded wires of these thin metal wires. It is preferable that the length of a forward traction wire and that of a rearward traction fiber are 10 to 80 mm. It is preferable that the diameters of these wires are 50 to 1000 μm.

The basic construction of the living body embryo transplanting device 1f of the embodiment shown in FIG. 25 is the same as that of the above-described living body embryo transplanting device 1. The difference therebetween is that the living body embryo transplanting device 1f into the uterus has the above-described linear member 57 for collection and the linear member insertion part 59 through which the linear member 57 for collection is inserted.

The living body embryo transplanting device 1f of this embodiment has a container transfer tool 5c for transferring the embryo accommodation container into the uterus. The container transfer tool 5c has the flexible sheath 2 and a flexible shaft 3c slidably inserted into the flexible sheath. The construction of the flexible sheath 2 is the same as the constructions of those described previously. The flexible shaft 3c has a hollow shaft body 31a and a hollow shaft hub 32a provided at a proximal end of the shaft body. The flexible shaft 3c has the linear member insertion part 59 penetrating therethrough from its distal end to proximal end. The linear member insertion part 59 is formed of a hollow part of the hollow shaft body 31a and a hollow part, of the hollow shaft hub 32a, which is continuous with the hollow part of the hollow shaft body 31a.

The linear member 57 for collection penetrates through the linear member insertion part 59. A proximal end portion of the linear member 57 for collection is extended to the outside from a rear end of the container transfer tool 5c, more specifically, a rear end of the flexible shaft 3c. The other end portion of the linear member 57 for collection extends from the living body in the state in which the container transfer tool has been pulled out of the living body after the embryo accommodation container 4e is disposed at the target portion of the living body (more specifically, inside uterus). Thus, by pulling the linear member 57 for collection after the embryo separates from the embryo accommodation container 4e (after embryo implants on uterus), it is possible to collect the embryo accommodation container 4e from the living body.

The shaft hub 32a of the flexible shaft 3c of this embodiment also has a cylindrical part 33a projecting toward the distal end of the flexible shaft 3c. The cylindrical part 33a is fixed to the proximal end of the shaft body 31a. Thus, the shaft body 31a is fixed to the hub 32a by means of the cylindrical part 33a. The cylindrical part 33a of the shaft hub 32a is slidable inside the sheath hub 23. The cylindrical part 33a of the shaft hub 32a and the sheath hub 23 have sliding resistance to some extent. Unless both are moved relatively to each other, it is possible to hold the state between both (for example, the state shown in FIG. 25).

The basic construction of the living body embryo transplanting device 1g of the embodiment shown in FIG. 26 is the same as that of the above-described the living body embryo transplanting device 1d into the uterus. The difference therebetween is that the living body embryo transplanting device 1g into the uterus has the above-described linear member 57 for collection and a groove portion 33d through which the linear member 57 for collection is inserted.

The living body embryo transplanting device 1g of this embodiment into the uterus has an embryo accommodation container 4f to which one end of the linear member 57 for collection is fixed and a container transfer tool 5g for holding the embryo accommodation container 4f at the distal end portion of container transfer tool. Except for the linear member 57 for collection, the construction of the embryo accommodation container 4f is the same as that of the embryo accommodation container 4d. The container transfer tool 5g has a flexible sheath 2d and a flexible shaft 3g slidably inserted into the flexible sheath 2d. The flexible shaft 3g has a shaft body 31d and a shaft hub 32g provided at a proximal end of the shaft body 31d. The container transfer tool 5g has a linear member insertion part. The linear member insertion part is constructed of a gap formed between an inner surface of the flexible sheath 2d and the flexible shaft 3g, a lumen of the sheath hub 23, and the groove portion 33d of the shaft hub 32g. The linear member 57 for collection penetrates the gap formed between the inner surface of the flexible sheath 2d and the flexible shaft 3g, the lumen of the sheath hub 23, and the groove portion 33d of the shaft hub 32g. A proximal end portion of the linear member for collection is extended to the outside from a rear end portion of the container transfer tool 5g.

In the living body embryo transplanting device 1g of this embodiment into the uterus, after the embryo accommodation container 4f is disposed at the target portion of the living body (specifically, inside uterus), the container transfer tool is pulled out of the living body. In this state, the other end portion of the linear member 57 for collection is extended from the living body. Thus, by pulling the linear member 57 for collection after the embryo separates from the embryo accommodation container 4f (after embryo implants on uterus), it is possible to collect the embryo accommodation container from the living body.

In each of the living body embryo transplanting devices 1f and 1g of the above-described embodiments, the other portion of the linear member 57 for collection is extended to the outside from the container transfer tool. In the instrument, for fixedly transplanting the living body embryo into the uterus, which has the above-described construction, it is easy to check the presence of the linear member 57 for collection, which is preferable. But the instrument for fixedly transplanting the living body embryo into the uterus may have a construction in which the other portion of the linear member 57 for collection is accommodated inside the container transfer tool and is exposed when the container transfer tool is pulled out of the living body.

Figure 28:
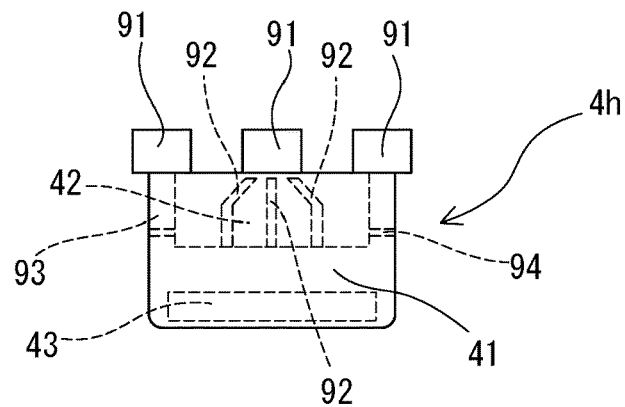
FIG. 28 is an enlarged front view of an embryo accommodation container of still another embodiment for use in the instrument of the present invention for fixedly transplanting the living body embryo into the uterus.
Figure 29:
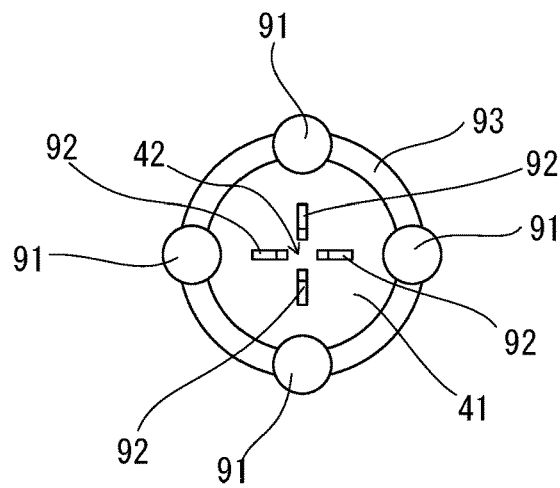
FIG. 29 is a plan view of the embryo accommodation container shown in FIG. 28.
Figure 30:
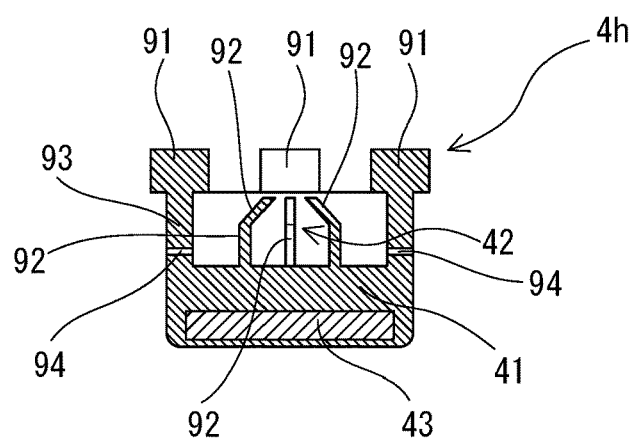
FIG. 30 is a vertical longitudinal sectional view of the embryo accommodation container shown in FIG. 28.

As the embryo accommodation container for use in the instrument of the present invention for fixedly transplanting the living body embryo into the uterus, it is possible to use an embryo accommodation container 4h shown in FIGS. 28 through 30. The basic construction of the embryo accommodation container 4h of this embodiment is the same as that of the above-described embryo accommodation container 4.

As shown in FIGS. 28 through 30, the embryo accommodation container 4h has a plurality of attaching leg parts 91 to be attached to the endometrium. The body part 41 of the embryo accommodation container 4h of this embodiment has a cylindrical part 93. The body part has a plurality of leg parts 91 projecting from a distal end of the cylindrical part 93. Each of the leg parts 91 is formed substantially columnarly. An outer side portion of the leg part 91 projects outward from an outer side surface of the cylindrical part 93. An inner side portion of the leg part 91 projects inward from an inner side surface of the cylindrical part 93. It is preferable that the number of the leg parts 91 is three to eight.

The body part 41 has a plurality of embryo-holding claw portions 92 projecting upward on its inner bottom surface. The embryo-holding claw portions 92 are curved inward at distal end portions thereof, thus forming the embryo accommodation part 42 inside the claw portions. Thus, in the embryo accommodation container 4h of this embodiment, the embryo accommodation part 42 is positioned inside the cylindrical part 93 and is not exposed. It is preferable that the number of the embryo-holding claw portions 92 is three to eight. As shown in FIG. 30, the embryo accommodation container 4h has at least two flow paths (communication path) 94 provided at the cylindrical part 93. Thus, the circulation of a culture fluid to the embryo accommodated inside the embryo accommodation part 42 is favorable.

As with the above-described embryo accommodation container 4, the embryo accommodation container 4h has the magnetic material 43. The embryo accommodation container 4h is formed of synthetic resin inside which the magnetic material 43 is embedded. The magnetic material 43 may be fixed to a lower surface of the embryo accommodation container 4h. As the magnetic material 43, it is possible to suitably use those described above.

Figure 31:
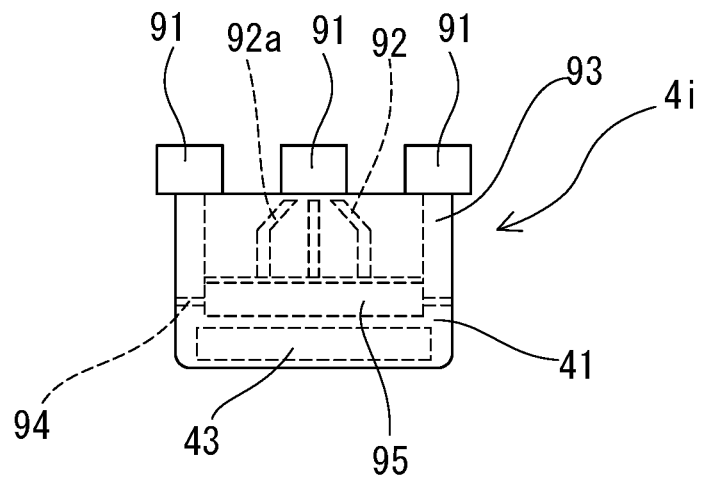
FIG. 31 is an enlarged front view of an embryo accommodation container of still another embodiment for use in the instrument of the present invention for fixedly transplanting the living body embryo into the uterus.
Figure 32:
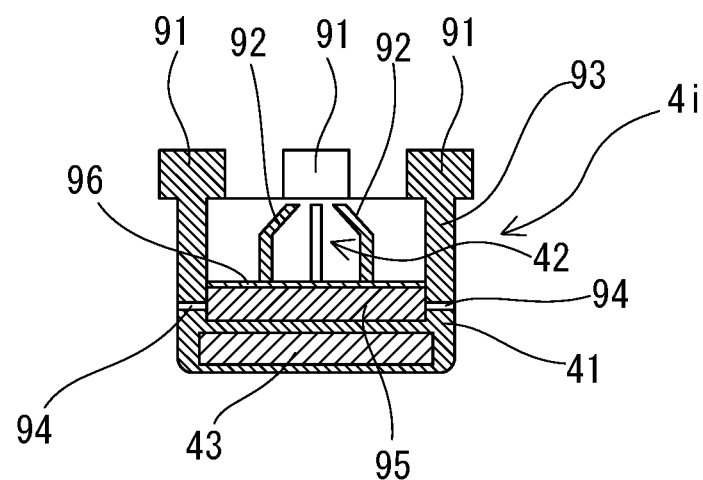
FIG. 32 is a vertical longitudinal sectional view of the embryo accommodation container shown in FIG. 31.

As the embryo accommodation container for use in the instrument of the present invention for fixedly transplanting the living body embryo into the uterus, it is possible to use an embryo accommodation container 4i shown in FIGS. 31 and 32. The basic construction of the embryo accommodation container 4i of this embodiment is the same as that of the above-described embryo accommodation container 4h.

As shown in FIGS. 31 and 32, the embryo accommodation container 4i has a plurality of attaching leg parts 91 to be attached to the endometrium. The body part 41 of the embryo accommodation container 4i of this embodiment also has the cylindrical part 93. The body part 41 has a plurality of leg parts 91 projecting from the distal end of the cylindrical part 93. Each of the leg parts 91 is formed substantially columnarly. The outer side portion of the leg part 91 projects outward from the outer side surface of the cylindrical part 93. The inner side portion of the leg part 91 projects inward from the inner side surface of the cylindrical part 93. It is preferable that the number of the leg part 91 is three to eight.

The body part 41 has a water-absorbing portion 95 inside it. The water-absorbing portion 95 has a flat plate portion 96 formed on an upper surface of the water-absorbing portion 95. It is preferable that the flat plate portion 96 is an elastic body and is water-permeable. As the flat plate portion 96, a flat plate member having an elastic membrane material and a water flow hole is suitably used. The water-absorbing portion 95 can be formed by filling a water-absorptive material into the body part 41. It is preferable to wrap the water-absorptive material with a water-permeable packaging material. As the water-absorptive material, known materials can be used. As the water-absorptive material, it is possible to suitably use at least one kind of a water-swelling polymer compound selected from among the group consisting of (meth)acrylic acid-based materials, polyvinyl alcohol-based materials, (meth)acrylic amide-based materials, polyalkylene oxide-based materials, polyalkylene imine-based materials, starch-based materials, and cellulose-based materials. It is also possible to suitably use at least one kind of the water-swelling polymer compound selected from among the group consisting of acrylate-based starch-grafted products, partly saponified polyvinyl alcohol, polyacrylates, acrylic acid-vinyl alcohol copolymers, polyethylene oxide, cellulose-based polymers, crosslinked N-vinyl carboxylic acid amide resin, polyethylene oxide-based polymers, pregelatinized starch, starch•sodium acrylate graft copolymers, isobutylene-maleic anhydride copolymers, and modified acrylic cross-linked polymers.

The flat plate portion 96 has a plurality of embryo-holding claw portions 92 projecting upward on an upper surface of the flat plate portion. The embryo-holding claw portions 92 are curved inward at distal end portions 92a thereof, thus forming the embryo accommodation part 42 inside the claw portions 92. Thus, in the embryo accommodation container 4i of this embodiment, the embryo accommodation part 42 is positioned inside the cylindrical part 93 and is not exposed. It is preferable that the number of the embryo-holding claw portions 92 is three to eight. As shown in FIG. 32, the embryo accommodation container 4i has at least two flow paths 94 provided at the cylindrical part 93 (more specifically, lower portion of cylindrical part 93). Thus, the circulation of a culture fluid to the water-absorbing portion 95 is favorable. As the flat plate portion 96, a water-absorptive membrane material is preferably used. As with the above-described embryo accommodation container 4h, the cylindrical part 93 of the embryo accommodation container 4i of this embodiment may be provided with the flow path (communication path) 94 communicating with the embryo accommodation part 42. It is preferable to form a small number of communication path.

As with the above-described embryo accommodation container 4, the embryo accommodation container 4i has the magnetic material 43. The embryo accommodation container 4i is formed of synthetic resin inside which the magnetic material 43 is embedded. The magnetic material 43 may be fixed to a lower surface of the embryo accommodation container 4i. As the magnetic material 43, it is possible to suitably use those described above.

Figure 33:
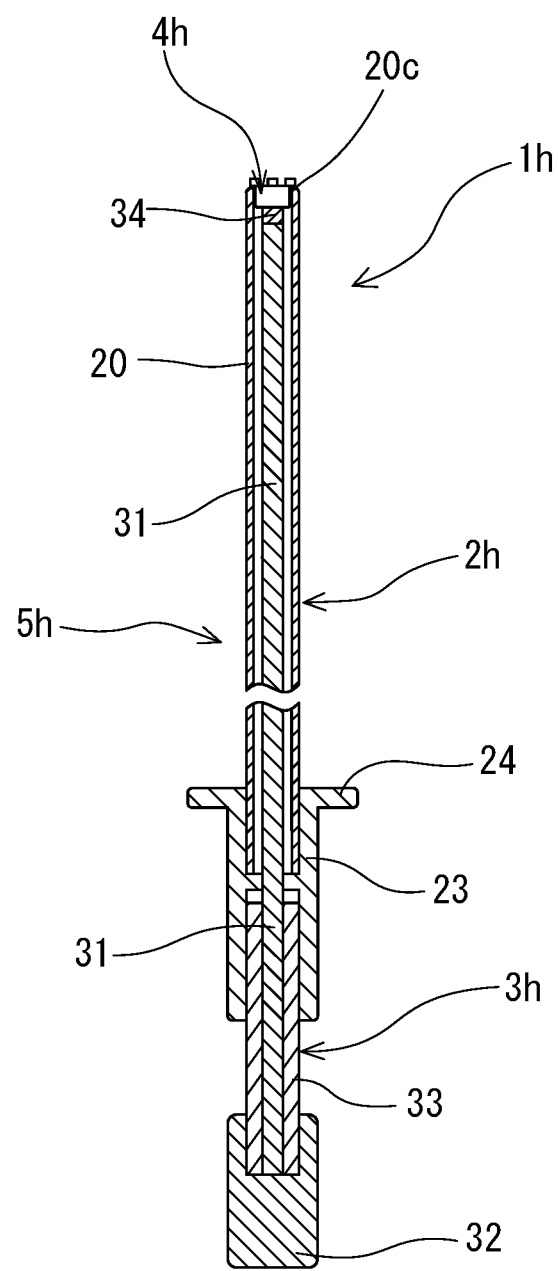
FIG. 33 is a vertical longitudinal sectional view of a living body embryo transplanting device of still another embodiment, which is used for the instrument of the present invention for fixedly transplanting the living body embryo into the uterus.

As a living body embryo transplanting device into the uterus, which uses the above-described embryo accommodation container 4h or 4i, a living body embryo transplanting device 1h into the uterus, as shown in FIG. 33, is suitable. The basic construction of the living body embryo transplanting device 1h into the uterus is the same as that of the above-described living body embryo transplanting device 1 into the uterus. The living body embryo transplanting device 1h into the uterus has the embryo accommodation container 4h and a container transfer tool 5h holding the embryo accommodation container 4h at the distal end portion of the embryo accommodation container. As the embryo accommodation container for use in the living body embryo transplanting device 1h into the uterus, the above-described embryo accommodation containers 4h and 4i are suitable.

In the container transfer tool 5h of this embodiment, a flexible sheath 2h has the container accommodation part for accommodating the body part 41 of the embryo accommodation container 4h or 4i at the distal end portion of the flexible sheath 2h. The flexible sheath 2h has the flexible outer tube 20. The sheath hub 23 is fixed to the proximal end of the outer tube 20. The sheath hub 23 has the gripping part. The above-described materials are used as materials for forming the flexible sheath 2h (outer tube 20).

The flexible shaft 3h has the shaft body 31, the permanent magnet 34 fixed to the distal end of the shaft body 31, and the shaft hub 32 provided at the proximal end of the shaft body 31. As materials for forming the shaft body 31, those described above are used. The flexible shaft 3h is provided with the permanent magnet 34 so that the permanent magnet attracts the magnetic material 43 of the embryo accommodation container 4 thereto. As the permanent magnet, the ferrite magnet, the neodymium magnet, the platinum magnet, the alnico magnet, and the samarium cobalt magnet are preferable.

In the flexible shaft 3h of this embodiment, the shaft hub 32 has the cylindrical part 33 projecting toward the distal end of the shaft 3h. The cylindrical part 33 is fixed to the proximal end of the shaft body 31. Thus, the shaft body 31 is fixed to the hub 32 by means of the cylindrical part 33. The cylindrical part 33 of the shaft hub 32 is slidable inside the sheath hub 23. The cylindrical part 33 of the shaft hub 32 and the sheath hub 23 have sliding resistance to some extent. Unless the cylindrical part of the shaft hub and the sheath hub are moved relatively to each other, it is possible to hold the state between both (for example, the state shown in FIGS. 33 and 34).

Figure 34:
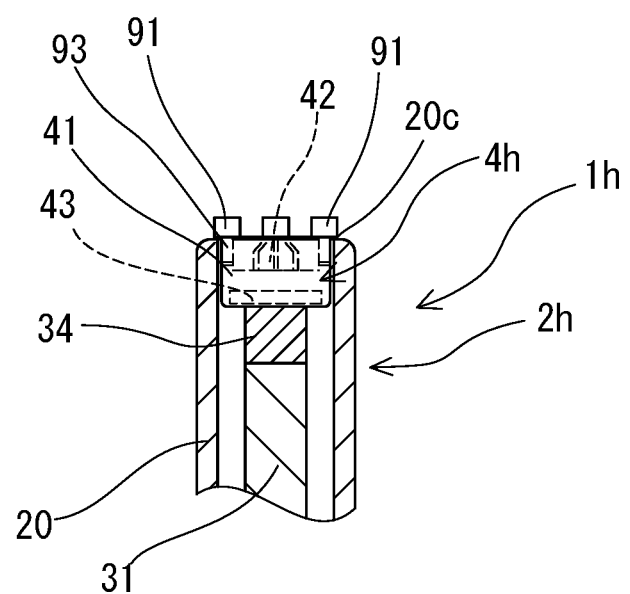
FIG. 34 is a distal end portion-enlarged view of the living body embryo transplanting device shown in FIG. 33.

The container transfer tool 5h has a state shown in FIG. 34. More specifically, in the container transfer tool 5h, the body part 41 of the embryo accommodation container 4h is accommodated inside the distal end of the sheath (container accommodation part), and the embryo accommodation container 4h is attractively held by the permanent magnet 34 of the shaft 3h. As shown in FIG. 34, the attaching leg parts 91 provided on the distal end surface of the cylindrical part of the body part 41 of the embryo accommodation container 4h is incapable of penetrating into the outer tube 20 of the flexible sheath 2h, in other words, into the container accommodation part. A part of a rear end surface of each of the attaching leg parts 91 of the embryo accommodation container 4h is capable of contacting a distal end surface 20c of the outer tube 20 of the flexible sheath 2h. The attaching leg parts 91 of the embryo accommodation container 4h are exposed from the distal end of the flexible sheath 2h.

As shown in FIG. 34, as with the above-described other container transfer tools, in the container transfer tool 5h of this embodiment, the embryo accommodation container 4h is accommodated inside the container accommodation part 25 with the embryo accommodation part 42 being located at the distal end side of the embryo accommodation container. Thus, a rear end surface of the embryo accommodation container 4h (rear end surface of body part 41) is directed toward the distal end surface of the shaft body 31.

In the living body embryo transplanting device 1h (container transfer tool 5h) of this embodiment, a part of the rear end surface of each of the attaching leg parts 91 of the embryo accommodation container 4h is in contact with or capable of contacting the distal end surface 20c of the outer tube 20 of the flexible sheath 2h. Therefore, by pulling the flexible shaft 3h toward the proximal end of the container transfer tool, the attaching leg parts 91 of the embryo accommodation container 4h contact the distal end of the shaft body 31 and is prevented from moving. Thereby the embryo accommodation container 4h moves out of the flexible shaft 3h. Because the embryo accommodation container 4h is not held by the flexible sheath 2h, the embryo accommodation container moves out of the flexible sheath 2h.

INDUSTRIAL APPLICABILITY

The instrument of the present invention for fixedly transplanting the living body embryo into the uterus has the following form.

(1) In an instrument for fixedly transplanting a living body embryo into a uterus, said instrument for fixedly transplanting said living body embryo into said uterus comprises a living body embryo transplanting device having an embryo accommodation container and inserting into said uterus, and a magnetic embryo accommodation container holding device, to be attached to a living body, for magnetically attracting said embryo accommodation container thereto;

wherein said embryo accommodation container has an embryo accommodation part having an embryo insertion portion communicating with outside, and a magnetic material;

said living body embryo transplanting device into said uterus has a shaft-shaped container transfer tool for separably holding said embryo accommodation container at a distal end portion of said container transfer tool; and said magnetic embryo accommodation container holding device has an attaching part to be attached on a living body epidermis and a magnet capable of attracting said magnetic material of said embryo accommodation container.

In the instrument of the present invention for fixedly transplanting the living body embryo into the uterus, it is possible to dispose the embryo accommodation container accommodating the embryo at an appropriate portion inside the uterus by using the instrument for fixedly transplanting the living body embryo into the uterus. The embryo accommodation container which has moved out from the instrument for fixedly transplanting the living body embryo into the uterus is magnetically held at the appropriate portion inside the uterus by means of the magnetic embryo accommodation container holding device disposed on the surface of the living body. The embryo which has grown bigger than a blastocyst inside the embryo accommodation container escapes (in other words, moves out) from the embryo accommodation container by itself and sticks to the endometrium, thus implanting thereon.

The instrument of the present invention for fixedly transplanting the living body embryo into the uterus may have the following form:

(2) An instrument for fixedly transplanting a living body embryo into a uterus according to the above (1), wherein said container transfer tool has a flexible sheath and a flexible shaft slidably inserted into said flexible sheath.

(3) An instrument for fixedly transplanting a living body embryo into a uterus according to the above (2), wherein said flexible sheath has a container accommodation part for accommodating said embryo accommodation container at a distal end portion of said flexible sheath.

(4) An instrument for fixedly transplanting a living body embryo into a uterus according to any one of the above (1) through (3), wherein said container transfer tool has a flexible sheath, a flexible shaft slidably inserted into said flexible sheath, and a permanent magnet, for attracting said magnetic material of said embryo accommodation container thereto, which is provided inside a distal end portion of said flexible sheath or at a distal end portion of said flexible shaft.

(5) An instrument for fixedly transplanting a living body embryo into a uterus according to any one of the above (1) through (4), wherein said magnetic material of said embryo accommodation container is a permanent magnet.

(6) An instrument for fixedly transplanting a living body embryo into a uterus according to any one of the above (1) through (5), wherein said embryo accommodation container has said embryo insertion portion and an opening allowing an inside of said container and said outside to communicate with each other, wherein a width of said opening is smaller than a maximum diameter of said embryo insertion portion.

(7) An instrument for fixedly transplanting a living body embryo into a uterus according to any one of the above (1) through (6), wherein said magnetic material of said embryo accommodation container is formed of a large number of bubbles contained in a material forming said accommodation container.

(8) An instrument for fixedly transplanting a living body embryo into a uterus according to any one of the above (1) through (7), wherein said embryo accommodation container contains a large number of bubbles.

(9) An instrument for fixedly transplanting a living body embryo into a uterus according to the above (1), wherein said container transfer tool has a shaft, an electromagnet provided at a distal end portion of said shaft and being capable of attracting said magnetic material of said embryo accommodation container, and a power supply part for supplying an electric power to said electromagnet.

(10) An instrument for fixedly transplanting a living body embryo into a uterus according to any one of the above (1) through (9), wherein said magnetic embryo accommodation container holding device has a lower sheet, said magnet fixed to a lower surface of said lower sheet, and an adhesive surface provided on said lower surface of said lower sheet.

(11) An instrument for fixedly transplanting a living body embryo into a uterus according to any one of the above (1) through (9), wherein said instrument has a linear member for collection whose one end is fixed to said embryo accommodation container and whose other end is extended toward a rear end of said container transfer tool.

(12) An instrument for fixedly transplanting a living body embryo into a uterus according to the above (11), wherein said instrument has a linear member insertion part, and other end portion of said linear member is extended to the outside of said container transfer tool from a proximal end portion of said linear member insertion part.

(13) An instrument for fixedly transplanting a living body embryo into a uterus according to any one of the above (1) through (12), wherein said embryo accommodation container has a flow path for circulating a culture fluid to said embryo accommodation part.

The invention claimed is:

1. An instrument for fixedly transplanting a living body embryo into a living body having a uterus comprising,
    a living body embryo transplanting device having an embryo accommodation container configured to be inserted into said uterus, and a magnetic embryo accommodation container holding device configured to be attached to the living body for magnetically attracting said embryo accommodation container thereto;
    wherein said embryo accommodation container has a magnetic material and an embryo accommodation part having an interior configured to accommodate the living body embryo, the embryo accommodation part having an embryo insertion portion communicating the interior of the embryo accommodation part with outside of the embryo accommodation part;
    said living body embryo transplanting device has a shaft-shaped container transfer tool for separably holding said embryo accommodation container at a distal end portion of said container transfer tool; and
    said magnetic embryo accommodation container holding device has an attaching part configured to be attached to a living body epidermis and a magnet configured to attract said magnetic material of said embryo accommodation container.

2. An instrument for fixedly transplanting a living body embryo into a uterus according to claim 1, wherein said container transfer tool has a flexible sheath and a flexible shaft slidably inserted into said flexible sheath.

3. An instrument for fixedly transplanting a living body embryo into a uterus according to claim 2, wherein said flexible sheath has a container accommodation part for accommodating said embryo accommodation container at a distal end portion of said flexible sheath.

4. An instrument for fixedly transplanting a living body embryo into a uterus according to claim 1, wherein said container transfer tool has a flexible sheath, a flexible shaft slidably inserted into said flexible sheath, and a permanent magnet, for attracting said magnetic material of said embryo accommodation container thereto, which is provided inside a distal end portion of said flexible sheath or at a distal end portion of said flexible shaft.

5. An instrument for fixedly transplanting a living body embryo into a uterus according to claim 1, wherein said magnetic material of said embryo accommodation container is a permanent magnet.

6. An instrument for fixedly transplanting a living body embryo into a uterus according to claim 1, wherein said embryo accommodation container has said embryo insertion portion and an opening allowing an inside of said container and said outside to communicate with each other, wherein a width of said opening is smaller than a maximum diameter of said embryo insertion portion.

7. An instrument for fixedly transplanting a living body embryo into a uterus according to claim 1, wherein said magnetic material of said embryo accommodation container is comprised of particles of the magnetic material contained in a material forming said accommodation container.

8. An instrument for fixedly transplanting a living body embryo into a uterus according to claim 1, wherein said embryo accommodation container is made of a material that contains bubbles.

9. An instrument for fixedly transplanting a living body embryo into a uterus according to claim 1, wherein said container transfer tool has a shaft, an electromagnet provided at a distal end portion of said shaft and being capable of attracting said magnetic material of said embryo accommodation container, and a power supply part for supplying an electric power to said electromagnet.

10. An instrument for fixedly transplanting a living body embryo into a uterus according to claim 1, wherein said magnetic embryo accommodation container holding device has a lower sheet, said magnet fixed to a lower surface of said lower sheet, and an adhesive surface provided on said lower surface of said lower sheet.

11. An instrument for fixedly transplanting a living body embryo into a uterus according to claim 1, wherein said instrument has a linear member for collection for collecting said embryo accommodation container, the linear member for collection having one end fixed to said embryo accommodation container and an other end extended toward a rear end of said container transfer tool.

12. An instrument for fixedly transplanting a living body embryo into a uterus according to claim 11, wherein said instrument has a linear member insertion part through which the linear member for collection is inserted, the linear member insertion part including one end portion and an other end portion, the other end portion of said linear member insertion part is extended to outside of said container transfer tool from a proximal end portion of said linear member insertion part.

13. An instrument for fixedly transplanting a living body embryo into a uterus according to claim 1, wherein said embryo accommodation container has a flow path for circulating a culture fluid to said embryo accommodation part.

* * * * *